US008736287B2

(12) United States Patent
Dhirani et al.

(10) Patent No.: US 8,736,287 B2
(45) Date of Patent: May 27, 2014

(54) CONDUCTANCE DETECTION SYSTEM AND METHOD

(75) Inventors: Al-Amin Dhirani, Toronto (CA); Yoshinori Suganuma, Toronto (CA)

(73) Assignee: Universal Nanosensor Technologies Inc. (CA)

(*) Notice: Subject to any disclaimer, the term of this patent is extended or adjusted under 35 U.S.C. 154(b) by 411 days.

(21) Appl. No.: 13/255,077

(22) PCT Filed: Mar. 4, 2010

(86) PCT No.: PCT/CA2010/000310
§ 371 (c)(1),
(2), (4) Date: Nov. 21, 2011

(87) PCT Pub. No.: WO2010/099618
PCT Pub. Date: Sep. 10, 2010

(65) Prior Publication Data
US 2012/0056632 A1    Mar. 8, 2012

Related U.S. Application Data

(60) Provisional application No. 61/202,493, filed on Mar. 4, 2009.

(51) Int. Cl.
*G01R 27/08* (2006.01)
*G01N 33/50* (2006.01)

(52) U.S. Cl.
USPC .................... 324/692; 204/403.01

(58) Field of Classification Search
USPC .......... 324/692, 691, 649, 600; 600/547, 300, 600/481, 482; 204/228.6, 228.1, 194, 400, 204/403.01; 205/792, 775, 778.5, 779
See application file for complete search history.

(56) References Cited

U.S. PATENT DOCUMENTS

| 4,020,677 A | 5/1977 | Doddington et al. |
| 4,728,882 A | 3/1988 | Stanbro et al. |

(Continued)

FOREIGN PATENT DOCUMENTS

| CA | 1180759 | 1/1985 |
| CA | 2215164 | 6/1996 |

(Continued)

OTHER PUBLICATIONS

Haderka. Permittivity and Conductivity Detectors for Liquid Chromatography. Journal of Chromatography. Journal of Chromatography. Apr. 24, 1974. vol. 91. pp. 167-179.

(Continued)

*Primary Examiner* — Hoai-An D Nguyen

(57) ABSTRACT

A detection system and method for detecting one or a plurality of species from a mixture of species in a phase. The detection system and method detect changes in conductance induced by the species. The conductance includes a cell structure having a rigid architecture having a top surface a portion of which is electrically conductive forming a first conductive component. A second conductive component substantially overlaps the first conductive component and is spaced from the first conductive component by an insulating component. One or more flow pathways exist between the first conductive component and the second conductive component for the chemical and/or biological species to flow. A time dependent electrical signal for inducing a time dependent response is applied to at least one of said first and second conductive components and a signal detector coupled to at least one of the first and second conductive components measures the time dependent response.

30 Claims, 19 Drawing Sheets

(56) References Cited

U.S. PATENT DOCUMENTS

| | | | |
|---|---|---|---|
| 5,008,627 | A | 4/1991 | Tsutsuta et al. |
| 5,045,798 | A | 9/1991 | Hendrick |
| 5,082,627 | A | 1/1992 | Stanbro |
| 6,521,109 | B1 | 2/2003 | Bartic et al. |
| 6,548,311 | B1 | 4/2003 | Knoll |
| 6,847,216 | B2 | 1/2005 | Marszalek |
| 6,902,701 | B1* | 6/2005 | Hughes et al. .................. 422/83 |
| 8,065,904 | B1* | 11/2011 | Allendorf et al. ............ 73/31.06 |
| 2002/0070114 | A1 | 6/2002 | Miles |
| 2003/0141189 | A1 | 7/2003 | Lee et al. |
| 2004/0146909 | A1 | 7/2004 | Duong et al. |
| 2007/0209977 | A1 | 9/2007 | Wilf et al. |
| 2009/0142504 | A1* | 6/2009 | Ervin et al. ................ 427/430.1 |

FOREIGN PATENT DOCUMENTS

| | | |
|---|---|---|
| CA | 2267281 A1 | 4/1998 |
| CA | 2554997 A1 | 2/2005 |
| EP | 1376111 | 1/2004 |
| JP | 08313577 | 11/1996 |
| JP | 09033582 | 7/1997 |
| JP | 2007006858 A | 1/2007 |
| JP | 2007530413 A | 11/2007 |
| WO | 88/09499 | 12/1988 |
| WO | 9849549 | 11/1998 |
| WO | 99/28737 | 6/1999 |
| WO | 0017630 | 3/2000 |
| WO | 2007104163 A1 | 9/2007 |

OTHER PUBLICATIONS

Crabtree et al. Shah Convolution Fourier Transform Detection. Anal. Chem. 1999. 71-2130-2138.

McReynolds et al. Comparison of Hadamard Transform and Signal-Averaged Detection for Microchannel Electrophoresis. Anal. Chem. 2004. 76. 3214-3221.

McReynolds et al. Shah and Sine Convolution Fourier Transform Detection for Microchannel Electrophoresis with Charge Coupled Device. Anal. Chem. 2002. 74. 5063-5070.

Kwok et al. Characterisation of Shah Convolution Fourier Transform Detection. Analyst. 2001. 126. 1640-1644.

Eijkel et al. Wavelet Transform for Shah Convolution Velocity Measurements of Single Particles and Solutes in a Microfluidic Chip. Lab on a Chip. 2001. 1. 122-126.

Kaneta, T. Hadamard Transform CE. Anal. Chem. Oct. 8, 2001. pages.

Kwok et al. Shah Convolution Differentiation Fourier Transform for Rear Analysis in Microchip Capillary Electrophoresis. J. Chromatography A. 924. 2001. 177-186.

Nadherna et al. Properties of the Contactless Impedance Detector with Insulated Wire Electrodes Placed Inside the Flowing Liquid Stream. Electroanalysis 19. 2007. No. 23. 2413-2418.

Tanyanyiwa et al. High-Voltage Capacitively Coupled Contactless Conductivity Detection for Microchip Capillary Electrophoresis. Anal Chem. 74. 2002. 6378-6382.

Wang et al. Movable Contactless-Conductivity Detector for Microchip Capillary Electrophoresis. Anal. Chem. 2003. 75. 4475-4479.

Takeuchi et al. Use of a Capacitance Measurement Device for Surrogate Noncontact Conductance Measurement. Talanta. 76. 2008. 617-620.

Kuban et al. High-performance Liquid Chromatography with Contactless Conductivity Detection for the Determination of Peptides and Proteins Using a Monolithic Capillary Column. J. Chromatography A. 1176. 2007. 185-191.

Fu et al. Fabrication and Testing of High-performance Detection Sensor for Capillary Electrophoresis Microchips Biomed Microdevices. 2008. 10. 73-80.

Pumera, M. Contactless Conductivity Detection for Microfluidics Designs and Applications. Talanta. 74. 2007. 358-364.

Kuban et al. A Review of the Recent Achievements in Capactively Coupled Contactless Conductivity Detection Analytica Chimica Acta. 607. 2008. 15-29.

Matysik, F. Advances in Amperometric and Conductometric Detection in Capillary and Chip-based Eletrophoresis. Microchim Acta. 2008. 160. 1-14.

Kuban et al. Fundamental Aspects of Contactless Conductivity Detection for Capillary Electrophoresis. Part II: Signal-to-noise Ratio and Stray Capacitance. Eletrophoresis. 2004. 25. 3398-3405.

Kuban et al. Fundamental Aspects of Contactless Conductivity Detection for Capillary Electrophoresis. Part I: Frequency Behavior and Cell Geometry. Electrophoresis. 2004. 25. 3387-3397.

Karunanayake et al. Capacitive Sensors for In-Vivo Measurements of the Dielectric Properties of Biological Materials. IEEE Trans. On Instrmentation and Measurement. 37. No. 1. Mar. 1988. 101-105.

Brust et al. Self-Assembled Gold Nanoparticle Thin Films with Nonmetallic Optical and Electronic Properties. Langmuir. 1998. 14. 5425-5429.

Musick et al. Eletrochemical Properties of Colloidal Au-Based Surfaces. Multilayer Assemblies and Seeded Colloid Films. Langmuir. 1999. 15. 844-850.

Musick et al. Stepwise Construction of Conductive Au Colloid Multilayers from Solution. Chem. Mater. 1997. 9. 1499-1501.

Fishelson et al. Studies on Charge Transport in Self-Assembled Gold-Dithiol Films. Conductivity. Photoconductivity and Photoelectrochemical Measurements. Langmuir. 2001. 17. 403-412.

Tay et al. Floating Resistivity Detector for Microchip Electrophoresis. Electrophoresis. 2007. 28. 4620-4628.

Hu et al. The Integration of Gold Nanoparticles with Semiconductive Oligomer Layer for Development of Capacitive Immunosensor. Sensors and Actuators B. 106. 2005. 641-647.

Benningfield et al. A Commercially Available Dielectric Constant Detector for Liquid Chromatography and Its Applications. J. Chromatographic Sc. vol. 19. Mar. 1981. 9 pages.

Construction of a Permittivity Detector for Liquid Chromatography. Methods of Analysis of Drugs of Abuse. Special Ed. May 1972. 2 pages.

Haderka, S. Role of the Mobile Phase Permittivity in the Use of the Capacitance Detectors in Liquid Chromatography. J. Chromatography. 52. 1970. 213-220.

Haderka, S. Use of the Resonance Principle in the Permittivity Detectors for Liquid Chromatography. 54. 1971. 357-366.

Haderka, S. The Prospects of Selective Detection by Capacitance Detectors for Liquid Chromatography. J. Chromatography. 57. 1971. 181-191.

Fuller et al. On-line Process Liquid Exclusion Chromatography Applied to the Production of Styrene-Butadiene Copolymers. J. Chromatorgraphic Sc. 17. Dec. 1979. 661-665.

Stelzle et al. Sensitive Detection of Protein Adsorption to Supported Lipid Bilayers by Frequency-Dependent Capacitance Measurements and Microelectrophoresis. Biochimica et Biophysica Acta. 981. 1989. 135-142.

Wohltjen, H. Colloidal Metal-Insulator-Metal Ensemble Chemiresistor Sensor. Anal. Chem. 1998. 70. 2856-2859.

Joseph et al. Self-Assembled Gold Nanoparticle/Alkanedithiol Films. Preparation Electron Microscopy. XPS-Analysis. Charge Transport and Vapor-Sensing Properties. J. Phys. Chem. B. 2003. 107. 7406-7413.

Joseph et al. Chemiresistor Coatings From Pt- and Au Nanoparticle/Nonanedithiol Films. Sensitivity to Gases and Solvent Vapors. Sensors and Actuators B. 98. 2004. 188-195.

Su et al. Miniaturized Chemical Multiplexed Sensor Array. J. Am. Chem. Soc. 2003. 125. 9930-9931.

Leopold et al. Growth Conductivity and Vapor Response Properties of Metal Ion-Carboxylate Linked Nanoparticle Films. Faraday Discuss. 2004. 125. 63-76.

Joseph et al. Gold-Nanoparticle/Organic Linker Films. Self-Assembly, Electronic and Structural Characterisation. Composition and Vapour Sensitivity. Faraday Discuss. 2004. 125. 77-97.

(56) References Cited

OTHER PUBLICATIONS

Di Carlo, D et al., "Nanogap-based dielectric immunosensing", Transducers, Solid-State Sensors, Actuators and Microsystems, 12th International Conference on, 2003, Piscataway, NJ, USA, IEEE, vol. 2, Jun. 9, 2003, pp. 1180-1183, XP010647611, ISBN: 978-0-7803-7731-8.

Yi M et al., "Theoretical and experimental study towards a nanogap dielectric biosensor", Biosensors and Bioelectroncis, Elsevier BV, NL, vol. 20, No. 7, Jan. 15, 2005, pp. 1320-1326, XP27619288, ISSN: 0956-5663.

European Search Report (EP 10 74 8270.5-1554) dated Feb. 15, 2013.

* cited by examiner

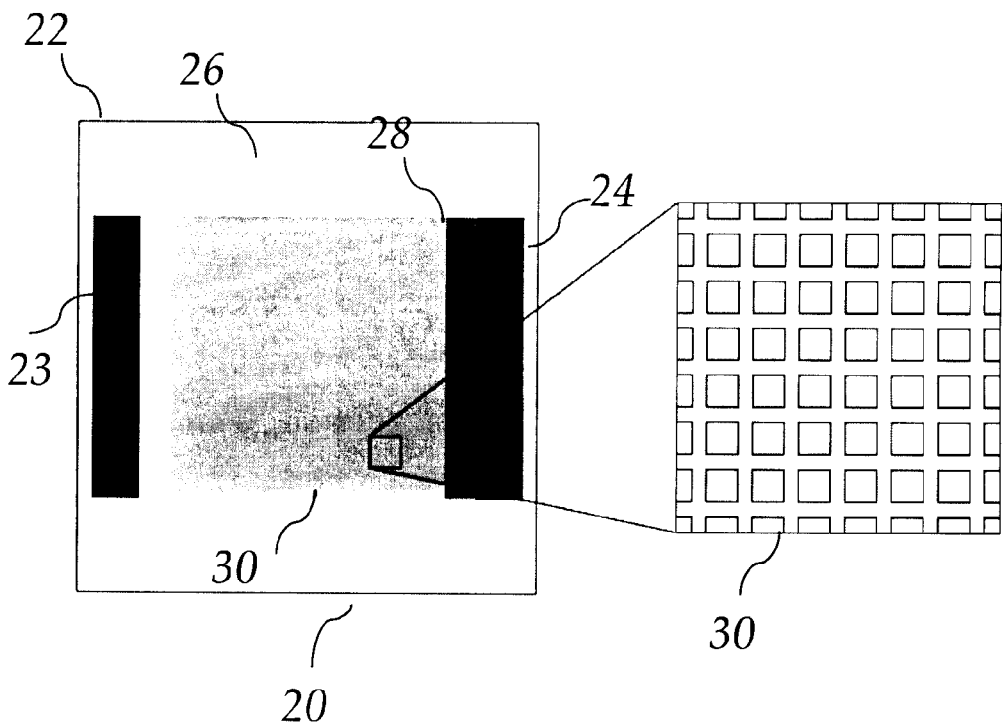
*Figure 2a*  *Figure 2b*
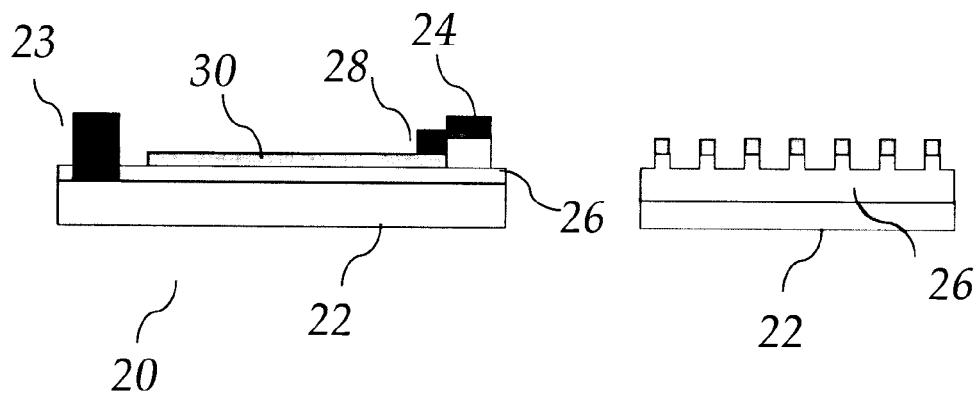
*Figure 2c*  *Figure 2d*

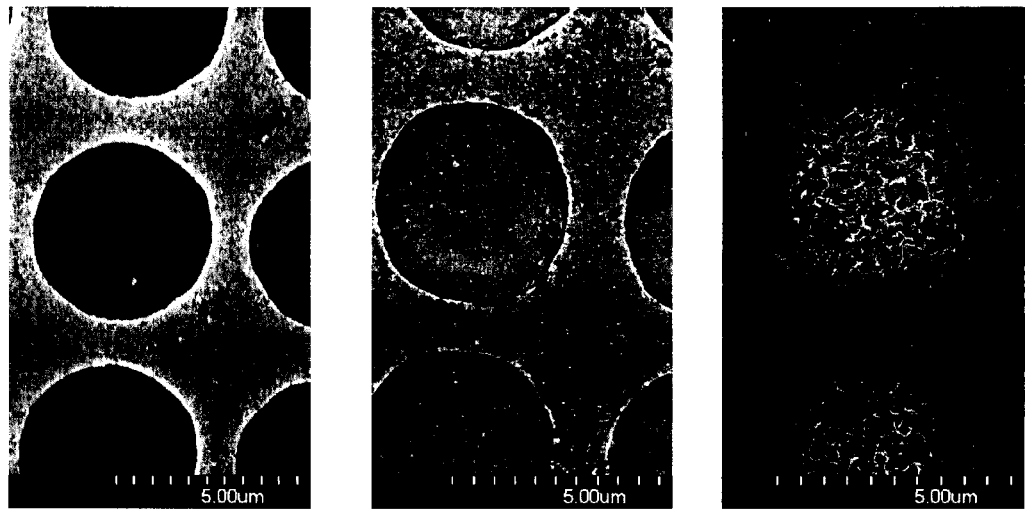
*Figure 2e*
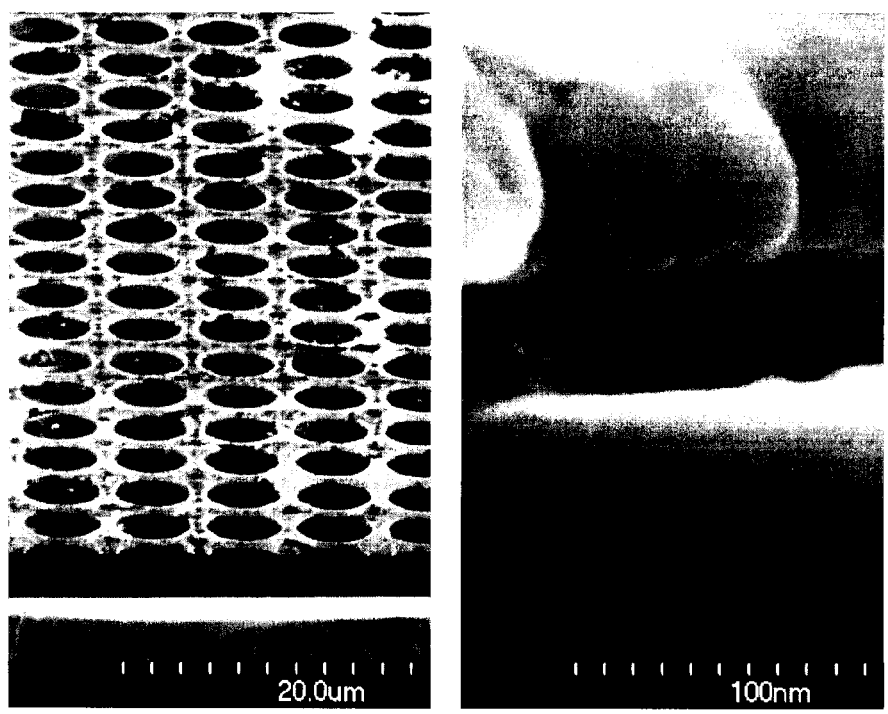
*Figure 2f*  *Figure 2g*

90

91

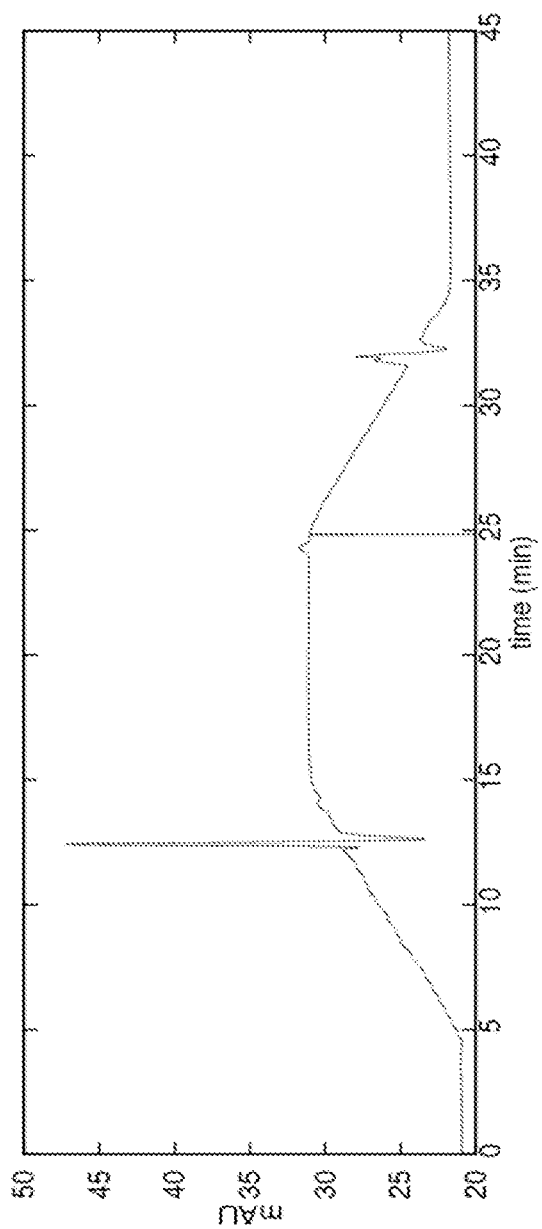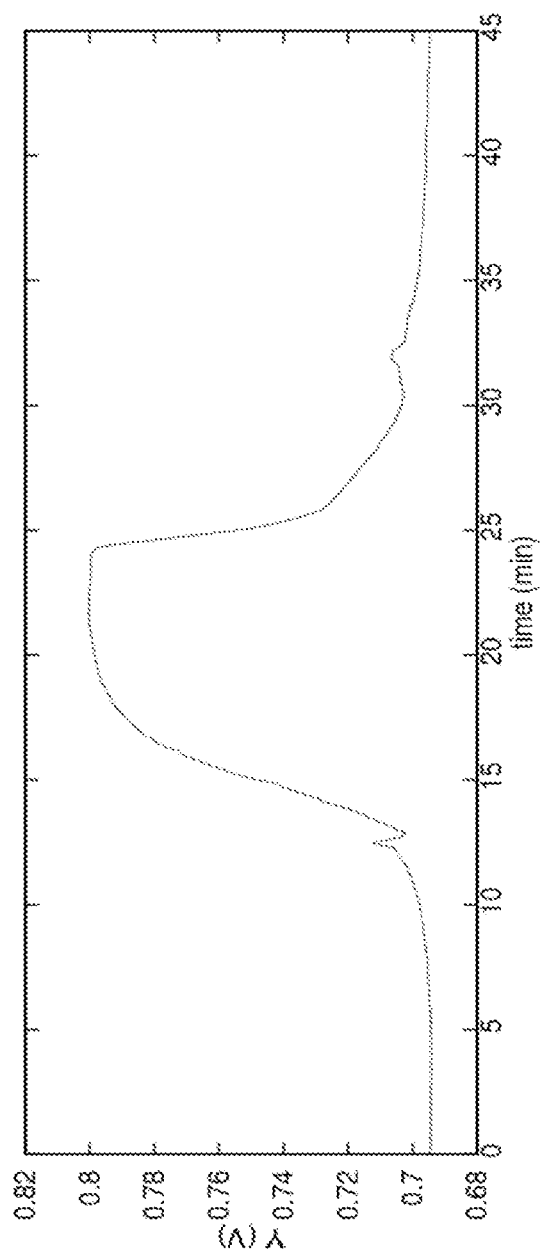
Fig. 10a
Fig. 10b

CONDUCTANCE DETECTION SYSTEM AND METHOD

CROSS-REFERENCE TO RELATED APPLICATION

This application is a National Phase application claiming the benefit of PCT/CA2010/000310 filed on Mar. 4, 2010, in English, which further claims priority to U.S. Provisional Application No. 61/202,493, filed on Mar. 4, 2009, the entire contents of which are incorporated herein by reference.

FIELD OF THE INVENTION

The present invention relates to a method and device for detecting the presence of chemical and/or biological target analytes of interest using conductance detection.

BACKGROUND OF THE INVENTION

Conductance detection systems and methods may be used in a wide variety of applications—one important example being separation methods and apparatus. Separation methods and apparatus are important in many contexts, including in the fundamental sciences such as chemistry, biology, environmental sciences, and the like as well as in industries relating to pharmaceuticals, health, chemicals, petroleum, food and the like. By using a separation method and apparatus, a sample mixture comprising a plurality of species is converted into two or more distinct products.

Many variations of separation methods and related apparatus are well known in the arts. By way of example, they may involve transporting a sample mixture using a mobile phase, which may be a liquid or a gas as in chromatography. Different species may be separated based on their interaction with a stationary phase, which may be disposed in a substantially columnar, capillary or planar geometry. By way of another example, if species in a sample mixture are charged, they may also be transported by an electric field, and different species may be separated based on their respective mobilities, as in electrophoresis. Varieties of electrophoretic separation methods and apparatus include those based on gels, capillaries, micro channels, 2-dimensional separations, etc. By way of yet another example, a species in a sample mixture in a liquid phase may be separated by being immobilized on a substrate, which then is removed from the sample mixture. This approach is central to many biosensors.

As various species are separated, there is a need to detect them for a variety of reasons, e.g. to evaluate the degree of separation (or lack thereof), to analyze them with respect to their quantity and their other properties, to aid in their isolation potentially for further processing or use, etc. Various types of detectors have been employed in this regard. With respect to separation methods and apparatus in which sample mixtures of species are carried by a liquid mobile phase, the most widely used detectors are based on optics. For species that have a significant absorbance in the ultra-violet to visible (UV-Vis) range of the electromagnetic spectrum, UV-Vis absorption spectroscopy may be employed.

It is noteworthy, however, that many important species such as carbohydrates, alcohols, and certain important polymers (for example, polyethylene glycol) do not have significant UV-Vis absorption. Further, application of UV-Vis spectroscopy to capillary electrophoresis, in particular, is challenging since UV-Vis absorbance is proportional to a path length over which light and a sample mixture interact but there is a desire to make capillary diameters small in order to yield improved separations.

The next most widely used type of detector is based on refractive index, that is, the ratio of the speed of light in a material relative to that in vacuum. Since index of refraction is a universal property of matter, even species that have no UV absorption are detectable. However, when detecting species that are good UV absorbers, UV-Vis detectors have much better sensitivity than index of refraction detectors. Also, index of refraction detectors are sensitive to temperature and require suitably controlled temperature environments.

Given a choice of various liquid mobile phases, if the composition of the liquid mobile phase is varied to elute a species from a column (as in gradient elution in high performance liquid chromatography or HPLC), the index of refraction of the solvent changes significantly, making additional potentially small changes in index of refraction due to species eluting from the column difficult to detect. That is, the large change in background due to changing solvent composition requires that the detector have a large dynamic range (achieved by coarse resolution). As a result, after this large change in background is subtracted from the data, smaller changes due to species have poor signal-to-noise. Incompatibility of refractive index detectors with gradient elution is a significant limitation hampering more wide spread application of refractive index detectors. In another optics-based approach, species may be excited (e.g. by a laser), and fluoresced light emitted by the species may be detected.

In cases where a species neither has significant UV-Vis absorbance nor generates significant fluorescence, the species may be chemically modified to increase its UV-Vis absorbance or fluorescence. This requires additional chemical processing steps, which can be undesirable due to a need for additional input of resources. Such additional chemical processing are common place, for example, when using thin layer chromatography or gel electrophoresis, and they may require significant additional processing time that is on the order of the time required to perform a separation itself. Furthermore, generally, detection methods and apparatus based on optics tend to be costly and somewhat unwieldy, hindering portability.

Therefore, for these reasons and others, other detection apparatus and methods not based on UV-Vis absorbance, refractive index or fluorescence have been developed. With respect to separation methods and apparatus that employ a liquid mobile phase, these include detection apparatus and methods based on electrochemical current, evaporative light scattering and mass spectroscopy. If a species can be dissolved in an electrolyte solution and can be oxidized or reduced, an electrochemical detector can be used to detect the species via the current produced by oxidation or reduction.

If a species is much less volatile than a solvent in which it is dissolved, then evaporative light scattering detectors can be used. In this approach for detecting a species, the species is atomized and transported by a gas. As the solvent evaporates, species form fine particles in the gas and are detected by light scattering. In liquid chromatography-mass spectroscopy, usually, the solvent is much more volatile than the species. Often volatile acids, bases or buffers are included in the sample mixture, and the species exists as ions in the sample mixture. Electrospray ionization is used to generate charged droplets of a sample mixture. As the droplets evaporate, eventually charged species remain and are detected by a mass spectrometer.

While these various methods have found useful applications, they also have significant limitations. Use of conductivity detectors is restricted to solvents that possess a practically measurable conductivity. Important organic solvents widely used with HPLC, e.g. hexane, have conductivities that are too low to be practically measurable. Also, if electrodes that probe conductivity are in contact with the sample mixture, changes in conductivity at the electrode-sample mixture interface can undesirably influence the overall conductivity measured. Electrochemical detectors are restricted to species that can be oxidized or reduced and to electrolytic solutions. Evaporative light scattering requires use of solvents that are much more volatile than species in the sample mixture. Important volatile molecules, for example, low molecular weight polymers such as polyethylene glycol, can not be detected. Similar restrictions arise in the case of mass spectroscopy detectors.

Mass spectroscopy detectors also require successful ionization of species and are typically very costly. Further, a number of the above-described detectors comprise myriad components such as optics, vacuum components, magnets, gas supplies, diode array detectors and the like that are bulky, require careful alignment, and thus significantly limit portability of the detectors. They also tend to be costly. Therefore, an apparatus and method for detecting species in a sample mixture that can detect a wide range of species, can function using a wide range of solvents (including solvents with varying composition that are employed during gradient elution), are easily portable and are cost effective are desired.

Although separation methods and apparatus using liquid mobile phase are desirable given that species are frequently synthesized in liquids, gas chromatography and associated detectors may also be employed to separate species. In this case, the most common apparatus and methods for detecting species are based on flame ionization detection and thermal conductivity detection. Both are sensitive to a wide range of components, and both work over a wide range of concentrations. Flame ionization detectors are sensitive primarily to hydrocarbons, and are more sensitive to them than thermal conductivity detectors. However, a flame ionization detector has difficulty detecting water. Other detectors are sensitive only to specific types of substances, work well only in narrower ranges of concentrations, may have limited portability and may be very costly. Other methods and apparatus for detecting species using gas chromatography include those based on discharge ionization, electron capture, flame photometry, Hall electrolytic conductivity, helium ionization, a presence of nitrogen phosphorus, photo-ionization, pulse discharge ionization, thermal energy analysis and mass spectroscopy.

Methods and apparatus for detecting species based on conductance measurements (or equivalently impedance measurements) provide an alternative to the above mentioned methods and apparatus, respectively. Conductance detectors make use of electronics which can be fabricated inexpensively and which can be compact and portable. Also, electrodes used to measure conductance probe the conductance of regions dictated by geometrical factors including electrode sizes, shapes, relative positions, and relative orientations, all of which are controllable over a wide range of length scales, from a nanometer length scales to micron length scales to millimeter lengths scales and even larger length scales. Electrodes can be fabricated exploiting chemical methods, electron beam lithography, optical lithography, shadow mask methods, and other methods well known to those skilled the arts. As such, methods and apparatus based on conductance detections are conveniently compatible with methods and apparatus for microfluidics, respectively, which enable extremely low sample and solvent volumes, sharp detection peaks, efficient separations and significant cost savings. Furthermore, conductance detection is amenable to methods well known in the arts for improving signal-to-noise, including lock-in detection and the like.

In a conductance measurement, a drive (such as a current or voltage) is applied to one or more electrodes and induces a response (such as a voltage or current, respectively). The drive may vary in time or may be substantially time independent. The sample mixture is arranged to traverse a proximity of at least one of the electrodes. The electrodes and sample mixture may or may not be in direct electrical contact with each other. For example, if the drive is a voltage, the one or more electrodes may cause a so-called external current, $i_{ext}$, to flow across surface(s) of the one or more electrodes by inducing mobile charges to flow across the surface(s); and/or, the one or more electrodes may cause a displacement current, $i_{disp}$, to flow by charging or discharging as a function of time.

In a linear approximation, if a voltage difference, $\Delta V$, is applied between a pair of electrodes and no displacement current flows between the pair of electrodes, the external current that flows between the electrodes is proportional to $\Delta V$ and is given by $$i_{ext} = \Delta V G_\sigma. \tag{1}$$

If one neglects fringing effects, then $$G_\sigma = \sigma \int dA/L \tag{2}$$

where $G_\sigma$ is $\sigma$-conductance, $\sigma$ is conductivity and depends on type and concentration of species present, $dA$ is an element of cross section area through which the external current flows, and $L$ is the distance over which the external current flows through the element. More generally, $$G_\sigma = \sigma L_\sigma \tag{3}$$

where $L_\sigma$ has dimensions of length and increases both with increasing cross sectional area and decreasing distance over which current flows. From Equation (3), it is evident that $L_\sigma$ is a geometrical amplification factor for conductivity.

Also in a linear approximation, if a voltage difference, $\Delta V$, is applied between a pair of electrodes and no external current flows between the pair of electrodes, the displacement current that flows between the electrodes is proportional to $\Delta V$ and is given by $$i_{disp} = \Delta V G_\in. \tag{4}$$

If one neglects fringing effects, then $$G_\in = j\omega \in \int dA/L \tag{5}$$

where $G_\in$ is $\in$-conductance, $j$ is a complex number such that $j^2 = -1$, $\omega$ is the angular frequency of the voltage difference assumed to vary sinusoidally with time, $\in$ is a permittivity, $dA$ is an element of cross sectional area over which the displacement current flows, and $L$ is the distance over which the displacement current flows through the element. More generally, $$G_\in = j\omega \in L_\in \tag{6}$$

where $L_\in$ has dimensions of length and increases both with increasing cross sectional area and decreasing distance over which current flows. From Equation (6), it is evident that $L_\in$ is a geometrical amplification factor for permittivity.

For sufficiently small voltages, the above-mentioned linear approximations work very well. A response of a conductance detector can frequently be adequately modeled by a net conductance, G, that is given as a series/parallel combination of suitable $G_\sigma$'s and $G_\in$'s by elementary circuit theory. Current can be measured by methods and apparatus well known in the arts and, given $\Delta V$, G can be thereby determined.

$G_\in$ and/or $G_o$ may vary depending on the type and concentration of species interacting with the one or more electrode. Detectors relying substantially on $G_o$ to detect species require that a presence of the species results in a practically detectable conductance change. With respect to chromatography, such $G_o$ detectors are commercially available. However, frequently (for example, in liquid chromatography) one employs solvents (e.g. hexane) which have conductivities that are too low to be practically measurable; as a result, species in such solvents can not be detected.

It is noteworthy that species that are amenable to electrophoretic separation are necessarily charged, and sample mixtures typically induce practically measurable conductance changes. Kuban (2004), Matysik (2008), Kuban (2008) and Pumera (2007) provide recent reviews of conductance detectors that detect a presence of a species in a sample mixture being separated via capillary and microchip electrophoresis via changes the species induce in $G_o$. We refer to such detectors as $G_o$ detectors. $G_o$ detectors for capillary electrophoresis are generally classified according to whether or not electrodes are in direct electrical contact with the sample mixture. In the case that electrodes are in contact with the sample mixture, great care must be exercised to ensure that the electrodes to not adversely affect the forces that drive the species in the sample mixture. $G_o$ detectors for microchip electrophoresis may be similarly classified. They may also be classified according to whether electrodes are on-column (i.e. located on a separation channel in which species are separated), off column (i.e. located on a channel branching off a separation channel) or end-column (i.e. located at the end of the separation channel). As an exception to the latter classification, Wang (2003) disclosed electrodes that are movable along the separation channel and that, therefore, enable monitoring separation of species at various points along the separation channel. Clarke et al. in U.S. Pat. No. 5,194,133 disclose a microchip electrophoresis apparatus with an array of electrodes in contact with the sample mixture. However, the electrodes detect electrochemical current, rather than changes in $G_o$. Tanyanyiwa et al. (2002) disclose that a $G_o$ detector with electrodes separated by ~1 mm yields better signal when the separation channel is located ~0.2 mm rather than ~1 mm below the electrodes.

U.S. Pat. No. 4,301,401 by Roof and Benningfield teaches a dielectric constant detector having a sample cell and a reference cell to provide an electrical signal that is proportional to the concentration of a component being passed through the dielectric constant detector. The sample and reference cells are adjusted in such a manner that the capacitance of each cell is substantially equal when the same fluid is in both cells.

Electronic circuitry associated with each cell provides an output signal which has a frequency and which is a function of the capacitance of each cell, respectively. The two output signals are mixed to provide a difference frequency and the difference frequency is converted to a voltage to provide an electrical signal which is representative of the concentration of the particular species of the sample mixture which is passing through the sample cell. However, Benningfield et al. (1981) teach that the detector's oscillation quenches when an equivalent parallel resistivity of the solute/solvent becomes less than 0.27 MΩ-cm.

As a result, common solvents such as water can seldom be used due to impurities. The detector also can not be used with common buffers, salts or other electrolytic solutions. Further, the detector is incompatible with use of gradient elution. Also, the architecture of the conductance detector is not rigid. The mobile phase and sample mixture flow between capacitor plates such that changes in pressure and carrier flow rate cause undesirable and significant variations in $L_\in$. Variations in $L_\in$ caused by pressure make variations in ∈ caused by a species of interest more difficult to detect. Further, $L_\in$ disclosed by prior art are small.

M. Yi et al. (2005) disclose a nanogap dielectric biosensor with an area of 1.5 μm×4 mm and an electrode separation of 20 nm; that is, the geometrical amplification factor is 1.5 μm×4 mm/20 nm or 30 cm. S. Roy et al. (2009) disclose mass-produced nanogap sensor arrays for ultrasensitive detection of DNA. The sensors are 5 μm×5 μm in area and the electrodes have a separation of 5 nm. In these sensors, only fringe electric fields are accessible for sensing. Assuming the fields extend beyond the edges of the sensor on a length scale that is on the order of a few times the electrode separation, the geometrical amplification factor is a few times 4 edges×5 μm×5 nm/5 nm or a few times 20 μm. The 819 Advanced IC detector (a conductivity detector) sold by Metrohm possesses cell constants, defined by $$\text{Cell constant} = L/A, \quad (7)$$

that range from 13 to 21 cm$^{-1}$. The corresponding geometrical amplification factors range from 0.5 mm to 0.8 mm. Other conductivity detectors sold by Metrohm possess cell constants that range from 0.1 cm$^{-1}$ to 10 cm$^{-1}$ and corresponding geometrical amplification factors that range from 0.1 cm to 10 cm. Hollis et al in U.S. Pat. No. 5,846,708 disclose an optical and electrical apparatus for molecule detection. In FIG. 4 of this patent, they disclose a conductivity detector with electrodes that have footprints that do not overlap. Hence, sensing is performed by fringe fields, as shown in the figure. The geometrical amplification factor thus is a few times 50 lines×2 edges per line×100 μm×400 nm/400 nm or 1 cm. Such small geometrical amplification factors result in correspondingly small conductance changes caused by a presence of species and require correspondingly large amplification. Potentially small conductance changes are difficult to detect, may require careful post-signal processing and are generally vulnerable to noise.

Thus, there is generally a need for improved methods and detectors for measuring changes in conductance with much higher sensitivity than is currently available. Equations (3) and (6) indicate that increasing geometrical amplification factors can yield correspondingly improved methods and detectors for measuring changes in conductance. In principle, this can be accomplished by combining a large number of area elements increasing the cross-sectional area and by decreasing the length of the region interrogated by the electrodes.

Such methods and apparatus for detecting conductance changes would have many applications. For example, in planar gel electrophoresis, species such as proteins and DNA are separated in multiple tracks along with calibration species and are subsequently detected by staining. A method and apparatus for detecting conductance changes induced by species as they are separating would be desirable as they would not require staining, thereby saving resources, and could provide information about species as they separate in real-time. In chromatography, conductance detectors with large geometrical amplification factors could function as "universal" detectors as all species possess a dielectric constant. Also, they can provide superior sensitivity to charged species via conductivity measurements. Many such applications will be readily apparent to those skilled in the arts.

Therefore, it would be desirable to have a detector and method for detecting changes in conductance caused by a presence of a species in a sample mixture, such that the changes are detected with signal-to-noise that is enhanced by noise rejection means, are suitably insensitive to undesirable fluctuations caused by influences such as pressure, are amplified by suitably large geometrical amplification factors, and are compatible with fluidic systems having constrained geometries, such as capillaries and planar systems, such a planar electrophoresis. It is further desired that the detector be compatible with gradient elution and a variety of mobile phases, including water and mobile phases that may contain impurities, buffers, salts or other electrolytes.

SUMMARY OF THE INVENTION

It will be appreciated by those skilled in the arts that the invention described herein has many applications, including but not restricted to various separation methods and apparatus relating to chromatography (including gas, liquid, column, planar including thin layer, etc.), and electrophoresis (including microchannel, capillary, gel, etc.). Various embodiments of the invention are shown by way of illustration and do not limit the scope of the invention.

The present invention provides conductance detector for detecting conductivity and/or dielectric constant of one or more chemical and/or biological species in a phase, comprising:
  a cell structure including
    a rigid architecture having a top surface a portion of which is electrically conductive forming a first conductive component;
    a second conductive component substantially overlapping the first conductive component and spaced from said first conductive component by an insulating component;
    one or more flow pathways between the first conductive component and the second conductive component for the chemical and/or biological species to flow;
    the first conductive component, the second conductive component and the insulating component having an architecture selected to give:
      a cross sectional area over which a displacement current and/or external current flows that is on an order of about 1 $cm^2$; and
      a distance over which the displacement current and/or external current flows that is in a range from about nanometer to hundreds of microns and even higher;
  a power supply for generating a time dependent electrical signal for inducing a time dependent response, the power supply being coupled to at least one of said first and second conductive components;
  a signal detector coupled to at least one of said first and second conductive components for measuring the time dependent response; and
  and a microprocessor connected to said signal detector for determining changes in conductance caused by a presence of said chemical and/or biological species in said phase.

The present invention also provides a method for detecting conductivity and/or dielectric constant of one or more chemical and/or biological species in a phase, comprising:
  flowing a phase being tested for the one or more chemical and/or biological species through a cell structure, the cell structure including
    a rigid architecture having a first electrically conductive component separated from a second conductive component by an insulating component,
    one or more flow pathways between the first conductive component and the second conductive component for the chemical and/or biological species to flow,
    the first conductive component, the second conductive component and the insulating component having an architecture selected to give
      a cross sectional area over which a displacement current and/or external current flows that is on an order of about 1 $cm^2$; and
      a distance over which the displacement current and/or external current flows that is in a range from about nanometer to hundreds of microns and even higher;
  applying a time dependent electrical signal to at least one of said first and second conductive components for inducing a time dependent response; and
  measuring the time dependent response and determining from said time dependent response any changes in conductance caused by a presence of said chemical and/or biological species in said phase.

Another embodiment of the invention provides a conductance detector for detecting conductivity and/or dielectric constant of one or more chemical and/or biological species dispersed in a phase and separated by an integrated substantially planar gel electrophoresis apparatus, comprising:
  a first rigid architecture having a top surface a portion of which is electrically conductive forming a first conductive component, the first component being insulated from the phase;
  a second conductive component, the second component being insulated from the phase;
  a gel component through which displacement current generated by the first or second conductive components flows;
  flow pathways through the gel component for the chemical and/or biological species to flow;
  a power supply for generating a time dependent electrical signal for inducing a time dependent response, the power supply being coupled to at least one of said first and second conductive components;
  a signal detector coupled to at least one of said first and second conductive components for measuring the time dependent response and a processor connected to said signal detector for determining changes in conductance caused by a presence of said chemical and/or biological species in said phase; and
  a processor connected to said signal detector configured to determine changes in conductance caused by a presence of said chemical and/or biological species.

The present invention also provides a method for detecting conductivity and/or dielectric constant of one or more chemical and/or biological species dispersed in a phase and separated by an integrated substantially planar gel electrophoresis apparatus, comprising:
  flowing said phase containing the one or more chemical and/or biological species through a substantially planar electrophoresis gel component which is located between
    a first electrically conductive component, the first electrically component being insulated from the phase and a second electrically conductive component, the second electrically component being insulated from the phase;
  a gel component through which displacement current generated by the first or second conductive components flows;
  flow pathways through the gel component for the chemical and/or biological species to flow;
  applying a time dependent electrical signal for inducing a time dependent response at least one of said first and second conductive components wherein a displacement current is generated by the first or second conductive components flows;

measuring the time dependent response and processing the measured time dependent response for determining changes in conductance caused by a presence of said chemical and/or biological species in said phase.

Further features of the invention will be described or will become apparent in the course of the following detailed description.

BRIEF DESCRIPTION OF THE DRAWINGS

The invention will now be described by way of example only, with reference to the accompanying drawings, in which:

FIG. 2a is a schematic of a conductance detector in accordance with a preferred embodiment of the invention;

FIG. 2b is an enlarged view of a portion of the conductance detector shown in FIG. 2a;

FIG. 2c is a cross-sectional view of the conductance detector shown in FIG. 2a;

FIG. 2d is a cross-sectional view of the conductance detector shown in FIG. 2b;

FIG. 2e shows scanning electron micrographs of a conductance detector that, going from left to right, has been repeatedly subjected to a treatment that includes exposure to water;

FIG. 2f is a scanning electron micrograph of a conductance detector that has been subjected to a treatment that includes exposure to hydrofluoric acid;

FIG. 2g is a scanning electron micrograph of a cross-section of the conductance detector shown in FIG. 2f;

FIGS. 6c and f are top and bottom views of the flash column adaptor, respectively. FIGS. 6d and e are side views of the flash column adaptor;

FIGS. 10a and b show HPLC data obtained simultaneously using a UV-Vis detector and conductance detector, respectively. The mobile phase was composed of methanol and acetonitrile, and the fraction of methanol was varied from 100% to 0% to 100%. As the composition was varied, acetyl salicylic acid (50 µL, 10 µM) was injected, both as the fraction of methanol was increasing and decreasing;

DETAILED DESCRIPTION OF THE INVENTION

Generally speaking, the systems described herein are directed to methods and devices for detecting the presence of chemical and/or biological target analytes of interest using conductance detection. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to method and device for detecting the presence of chemical and/or biological target analytes of interest using conductance detection.

As used herein, the term "about", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region.

The present invention has a number of uses. The following are presented just by way of example and are not to be construed as limiting or defining the invention.

Figure 1A:
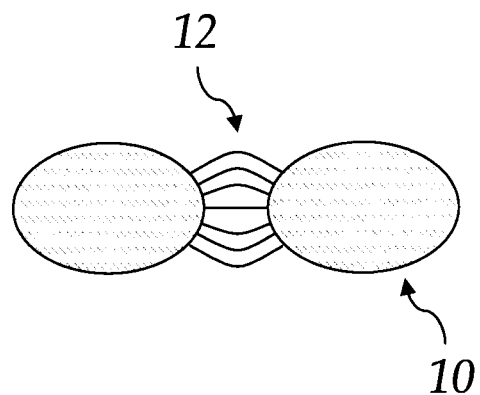
FIGS. 1a and b illustrate electric field lines between pairs of electrodes at two different inter-electrode separations.
Figure 1B:
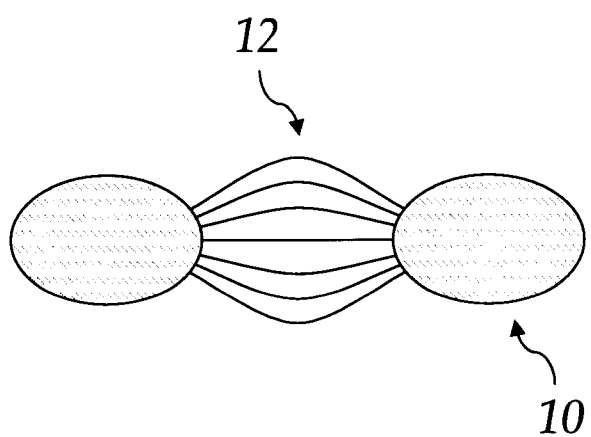

FIGS. 1a and 1b illustrate some aspects of the present invention. FIG. 1a shows a pair of electrodes 10 and some associated electric field lines 12 generated when a voltage is applied across the pair of electrodes 10. The electric field is strongest in a region between the pair of electrodes 10 and weakens at distances further away from the pair of electrodes.

The distance between the pair of electrodes 10 in FIG. 1b is larger than in FIG. 1a, and the field between the electrodes in FIG. 1a is correspondingly stronger than in FIG. 1b. Thus, FIGS. 1a and 1b as well as Eqns. 2 and 5 illustrate an aspect of the present invention, namely that a smaller electrode separation has a desirable effect of increasing geometrical factors of conductances (as defined in equations 3 and 6 above). With such increased geometrical factors, changes in conductances induced by species are correspondingly larger and can be measured with substantially higher signal-to-noise. This is desirable as it enables improved distinction between different species, detection of species at lower concentration, etc.

FIGS. 1a and 1b also illustrates that a characteristic length scale over which the fringing electric field weakens significantly is a function of the separation between electrodes. The fringing electric field weakens at distances further away from the electrodes more slowly in FIG. 1b than in FIG. 1a. Another aspect of the invention advantageously takes into consideration this effect of separation between electrodes on fringing electric fields as follows. If a species traverses a proximity of the electrodes 10, then it may cause a change in conductance at least in part induced by fringing electric fields.

If the separation between electrodes 10 is sufficiently small relative to the proximity of the species with respect to the electrodes 10, then the fringing electric fields may only sense a small portion or none of the species, which can be undesirable. At the same time, as the separation between electrodes becomes sufficiently large, the ability of the fringing fields to resolve the spatial distribution of the species diminishes significantly. For example, in a limit that the separation between electrodes becomes much larger than the size of the spatial distribution of species, the length scale over which the fringing fields sense the spatial distribution of species is substantially determined by the separation between electrodes rather than the spatial distribution of the species. It becomes more difficult to determine the size of the spatial distribution.

Furthermore, if there are a plurality of species, their spatial distributions may possess features, including a leading front, a trailing front, a maximum concentration, a half-maximum concentration, etc, and it may be desirable to resolve one or more of these spatial distribution features. For example, in many instances it may be desirable to resolve and characterize these features in order to determine the number of species present, the conductivity of the species, the concentration of the species, etc. As the resolution of these features increases, the earlier in a separation such determinations can be made, thus potentially saving considerable time, resources, cost, etc.

It is therefore desirable to provide a suitable spacing between electrodes such that the species traverse a proximity of the electrodes where the electric fields are sufficiently strong to detect the species. More preferably, the spacing is selected to resolve features of the detected species, and where the resolved features are characterized with sufficiently large signal-to-noise. For example, in situations where the species has been separated from a mixture earlier in a separation, the spatial features may be a spatial distribution of the species.

These aspects of the invention, along with others, are illustrated in various embodiments of the invention described below.

FIGS. 2a-2d show various views of a conductance detector 20 in one embodiment of the present invention. Conductance detector 20 includes a cell structure (through which the fluid being analyzed for the one or more chemical and/or biological species flows) which is fashioned on a rigid architecture 22 rendering the conductance detector resistant to deformations caused by environment influences (e.g. changes in pressure). Such deformations can cause geometrical amplification factors to change and in turn cause conductance to change undesirably. Various materials may be used as rigid architectures including glass, silicon, doped silicon, other semiconductors, metals, polymers, quartz, silica, alumina, composites, multilayered materials, etc. Insensitivity to undesirable influences of the environment due to changes in temperature, pressure, and the like is further aided by the fact that gradients are small due to symmetry between the mobile phase and the conductance detector; e.g., the mobile phase contacts, and preferably surrounds, the conductance detector during its operation.

Rigid architecture 22 comprises a first conductive. In a preferred embodiment of the invention, the resistance of the first conductive component 23 is not much larger than that of sample being probed. Otherwise, most of the applied voltage would be dropped across the first conductive component 23 rather than across the sample by a voltage divider effect; that is, the current generated across the sample (which contains information about the conductance of the sample) would be undesirably small.

In one embodiment, rigid architecture 22 itself is fashioned from an electrically conductive material (e.g. doped silicon, metal, conducting polymer, etc.) and forms the first conductive component as shown in FIG. 2a. In other embodiments, rigid architecture 22 has a conductive component or a plurality of conductive components on its top surface forming an electrode. A first of two contacts 23 electrically contacts the first conductive component.

In accordance with one aspect of the present invention, an electrically insulating component 26 covers at least a portion of the first conductive component 22. Insulating component 26 serves to space a second conductive component 30 and the first conductive component so as the prevent them from shorting. The thickness and architecture of the insulating component also provide a means for controlling the geometrical amplification factor of the conductance detector since the geometrical amplification factor is related to a ratio of a surface area over which an electrical current can flow to a distance over which the electrical current can flow.

Further, the insulating component tunes the degree to which the conductance detector functions as a sensor. If the insulating component is thin, the contribution of species that interact with the detector's surface become more significant, and the sensing capabilities of the detector improve. Functionalizing surfaces of the detector with chemical and/or biological species can provide information about species being sensed. The insulating component may be fashioned using a variety of materials such as inorganic materials e.g. silicon oxide, aluminum oxide, silicon nitride, silicon carbide, etc. or organic materials such as polymers, resists, and the like. Various choices for the insulating component are well known in the arts. In one embodiment of the invention shown in FIGS. 2a to 2d, the insulating component 26 is an oxide of rigid architecture 22. The insulating component may have different thicknesses in different regions of the conductance detector.

Methods for creating the insulating component 26 of various thicknesses in the sensing region are well known in the electronics arts. For example, insulating component 26 may be grown directly by exposing rigid architecture 22 that has a conductive component to a suitable reagent. For example, high quality oxides may be grown on silicon with Angstrom control with thicknesses that range from ~nanometer to hundreds of microns and even higher. Thus, while for many applications 40 nm may be preferred, thicknesses in the range from ~nanometer to hundreds of microns and even higher may be used depending on the application.

Alternatively, the insulating component 26 may be deposited, for example, using chemical vapour deposition, thermal deposition, spin coating, etc. In a contact region, the insulating component 26 may be thick enabling a second contact 24 to be placed on top and contacted to circuitry without electrically shorting to the first conductive component.

In accordance with another aspect of the present invention, in a sensing region, insulating component 26 is thin, potentially leading to desirably large geometrical amplification factors (as evidenced by equations 2 and 5). For example, with respect to the detector architecture shown in FIG. 2, a conductance detector that has an area that is on the order of ~1 square cm, an insulating component that is ~40 nm thick in the sensing region, a periodicity for the pattern shown of 6 µm, openings that are 3 µm and assuming the insulating component is undercut under the second conductive component by 100 nm, the conductance detector has a geometrical amplification factor that (given fringe electric fields) exceeds a number on the order of $(1 \text{ cm}/6 \text{ µm})^2 \times 4 \times 100 \text{ nm} \times 3 \text{ µm}/40 \text{ nm}$ or 80 m.

A second conductive component 30 is fashioned on top of insulating component 26. Second conductive electrode 30 may be contacted to second electrode 24 by intermediate contact 28. FIGS. 2b and 2d show magnified plan and cross-sectional views of the second conductive component, respectively. In the embodiment of the invention shown, the second conductive component comprises one or more openings. Under the application of a voltage between the first conductive component 22 and the second conductive component 30, electric field lines extend between the first conductive component 22 and the second conductive component 30. The openings provide species in a medium access to the electric field lines when the medium is contacted with at least the second conductive component.

In a preferred embodiment shown in FIG. 2b, the second conductive component 30 comprises two or more apertures exposing the underlying insulating component 26. The apertures enable sensing of the dielectric environment of the medium, resulting in a large geometrical amplification factor. In another embodiment, the second conductive component 30 comprises an interdigitated electrode. In still another embodiment of the invention, to generate still larger geometrical enhancement factors, the second conductive component may comprise one or a plurality of apertures with negligible areas through which species to be detected may enter, and the insulating layer may comprise at least one flow pathway through which species may flow. For example, for conductance detector with a first and second conductive components that are substantially overlapped, are parallel, and have a 1 $cm^2$ area and 100 nm separation, the geometrical enhancement factor would be 1 $cm^2$/100 nm or 1 km. In this preferred embodiment of the conductance detector, the detection volume is 0.1 µL, approximately 10 times smaller than that of UV-Vis detectors used in chromatography. The small detection volume and use of flow pathways lead to desirably narrow features in chromatographs. Those skilled in the art will readily appreciate that a wide variety of architectures for the conductive components and insulating component as well as flow pathways for the species may be utilized according to this embodiment of the invention.

In one embodiment, the conductive components 22 and 30 may be protected (for example, chemically protected) with an additional insulating layer (not shown). The conductance detector may be functionalized to reduce interaction between species being detected and the detector's surface, reducing tailing of features in chromatographs. The conductance detector may be functionalized to increase interaction between species being detected and the detector's surface, enabling kinetic studies of species adsorbing and/or desorbing from the surface. The insulating component 26 may also serve to prevent the potential applied between the electrodes 22 and 30 from detrimentally influencing separation of species in the sample mixture being sensed by the conductance detector. These various features and others may be implemented in accordance with an aspect of the invention to combine closely spaced, overlapping area elements of the first and second conductive components to generate a large geometrical amplification factor and improved signal-to-noise.

In accordance with an additional aspect of the present invention, the thickness of insulating component 26 can be well controlled, including in the sensing portion of the conductance detector 20. Consequently, the separation between the second conductive component 30 contacted by the second contact 24 and the first conductive component contacted by the first contact 23 as well as the regions sensed by electric fields can also all be desirably controlled, as discussed in the context of FIG. 1. To enhance the sensing capability of the conductance detector 20, the insulating component 26 may have flow paths as shown in FIGS. 2d to 2f, enabling species in a sample mixture to access the electric fields and be better sensed through the resulting increased geometrical amplification factors. The flow paths may be fashioned as the insulating component 26 is fashioned or by removing material afterwards (e.g. by chemical etching, ion etching, mechanical milling, sputtering, etc.).

As a first example, FIG. 2e shows a series of scanning electron micrographs of a conductance detector fabricated using standard lithographic methods well known in the arts. The first conductive and second conductive components are fashioned from silicon and aluminum, respectively, and the insulating component from a 40 nm thick silicon oxide layer. In this conductance detector, flow paths that improve sensitivity to species in a sample mixture have been formed through etching the aluminum by immersing the conductance detector in heated water. Going from left to right in FIG. 2e, as etching increases, pits form in the aluminum surface, and the circular apertures in the aluminum increase in size. Pits likely also form between the aluminum and the silicon oxide due to etching from the sidewalls of the apertures and the pits. Thus flow paths for species form, improving the geometrical amplification factor of the detector.

As a second example, FIGS. 2f and 2g, respectively, show top and cross-sectional scanning electron micrographs of another conductance detector with a second conductive component again formed from aluminum. The insulating component is fashioned from silicon oxide and is located between the second conductive component and a silicon conductive layer below which forms the first conductive component. In this conductance detector, flow paths that improve sensitivity to species in a sample mixture have been formed through etching with hydrofluoric acid. FIG. 2g shows that the acid has etched the insulating component downwards (exposing a portion of the top surface of the first conductive component) and sideways (undercutting the insulating component under the second conducting component).

Figure 2H:
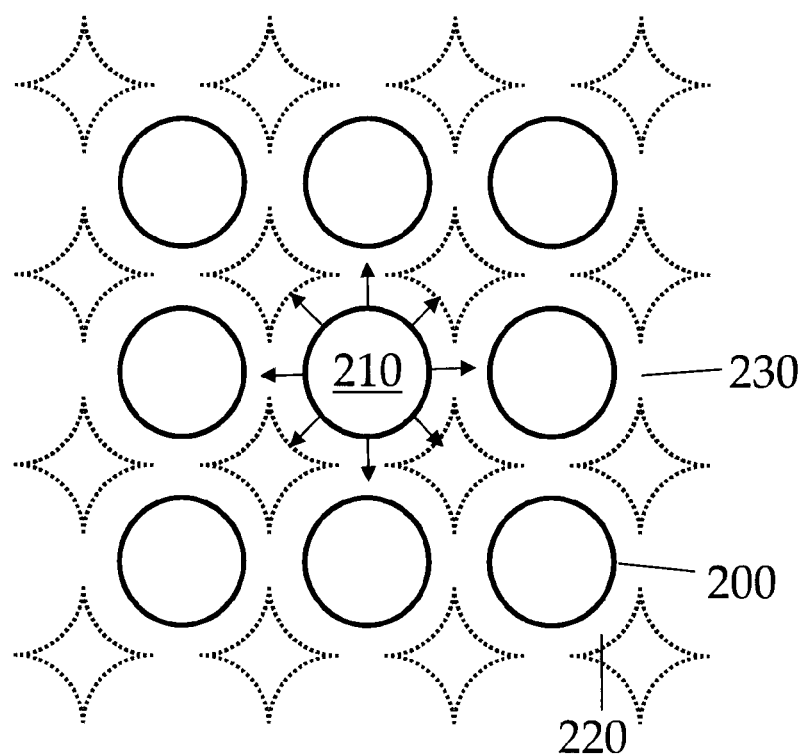
FIG. 2h is an illustration of a conductance detector with a connected network of pores between electrodes in accordance with a preferred embodiment of the invention.

As a third example, FIG. 2h shows a cross-section of a conductance detector in which flowpaths below the second conductive component are etched until they merge, forming a porous network beneath the second conductive component. Initially, flow paths 200 are provided, and subsequently etched, thus expanding 210 to form larger, connected flow paths 220 having connection via 230. This embodiment has the distinct advantage of providing a network through which species may be made to flow, thus greatly enhancing the interaction of the species with electric fields, and providing a sensitive detection platform.

Figure 2I:
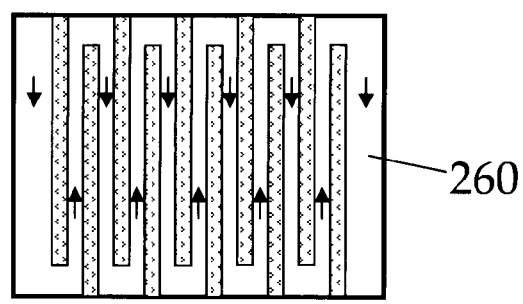
FIG. 2i is a view showing a conductance detector having one or a plurality of channels 260 through which the species can be made to flow.

As a fourth example, FIG. 2i shows that a conductance detector may have one or a plurality of channels 260 through which the species can be made to flow. It will be apparent to those skilled in the art that there are a variety of detector architectures that will permit species access to electric field lines generated by the conductive components in accordance with the present invention. For example, if the detector has one or a plurality of channels that are connected, the first conductive component may have one or a plurality of openings to permit species to enter the one or a plurality of connected channels and one or a plurality of openings to permit the species to exit. Alternatively, the species may gain access to the electric field lines through one or a plurality of gaps at edges of the first conductive component and the second conductive component. Many such examples of conductance detectors with increased geometrical amplification factors through the inclusion of flow paths (both isolated and interconnected) and means to allow species access to electric field lines in the flow paths will be readily apparent to those skilled in the arts.

In still another embodiment of the invention, the second conductive component comprises a plurality of interconnected electrode cells. In general, the electrode cells need not be similar to each other in terms of their size and/or shape, and they need not be periodically disposed with respect to each other. In the embodiment of the invention shown in FIG. 2, they all sense substantially a certain location within a fluidic environment, for example, a point of a separation process. Therefore, they can be combined by being interconnected leading to a large area, geometrical amplification factor and response. In still another embodiment of the invention, a plurality of unconnected electrode cells may be disposed at a plurality of known locations so that they detect at a plurality of points along a separation apparatus and generate a plurality of responses. The responses may then be combined in a variety of ways, effectively generating a large geometrical amplification factor and hence a large response.

For example, if the plurality of electrodes are periodically disposed and their responses are combined, a species moving at a constant velocity and being detected will contribute a periodic response to the combined response. A plurality of species traveling at a plurality of velocities will contribute a plurality of periodic responses with a plurality of periodicities to the combined response. The presence of the species may be clarified by fourier processing. In another embodiment of the invention, the plurality of responses may be combined by plotting them as a function of time and detector location. A plurality of species travelling at a plurality of uniform velocities will give rise to a plurality of linear features in the plot relative to background noise, enabling increased signal-to-noise. It will be readily apparent to those skilled in the arts that there are a variety of ways in which cell responses can be combined in order to improve signal-to-noise according to the fundamental teachings of Equations 2 and 5 to combine responses generated by area elements.

Another aspect of the present invention is that the conductance detector may be functionalized with at least one chemical or biological recognition element to enhance interaction between the conductance detector and species in the sample mixture. For example, to improve detection of a hydrophobic species, the conductance detector may be functionalized with a hydrophobic molecule such as an alkyl silane.

To accommodate the detection of an antigen, the conductance detector may be functionalized with a receptor such as an antibody or aptamer. Many such combinations are well known in the separation and assay arts. Such functionalized detectors may be referred to as sensors.

An advantageous aspect of this embodiment of the invention is that since the sensors are electronics based, they can be conveniently and cost-effectively multiplexed. As a result, a sample mixture may be sensed by a multiplicity of different sensors, each sensor potentially functionalized differently. In a preferred embodiment, species in the sample mixtures and the sample mixtures can, thus, be electronically "finger-printed" by the responses they produce using the multiplicity of different sensors.

By way of example, the multiplicity of sensors may be placed in series or in parallel within a chromatography apparatus to finger-print, and thereby, identify or otherwise characterize one or more species in a mixture or the mixture. Another advantageous aspect of the present invention is that the contribution of surface (sensor) effects can be controlled, not only by surface functionalization, but by geometry. By way of example, if the thickness of the insulating component 26 electrical signal between the second conductive component 30 and the first conductive component 22 increases, volume effects become stronger and surface effects weaker. This may be desirable for detectors. On the other hand, if the thickness decreases, surface effects become stronger and volume effects weaker. This may be desirable for sensors.

Figure 3:
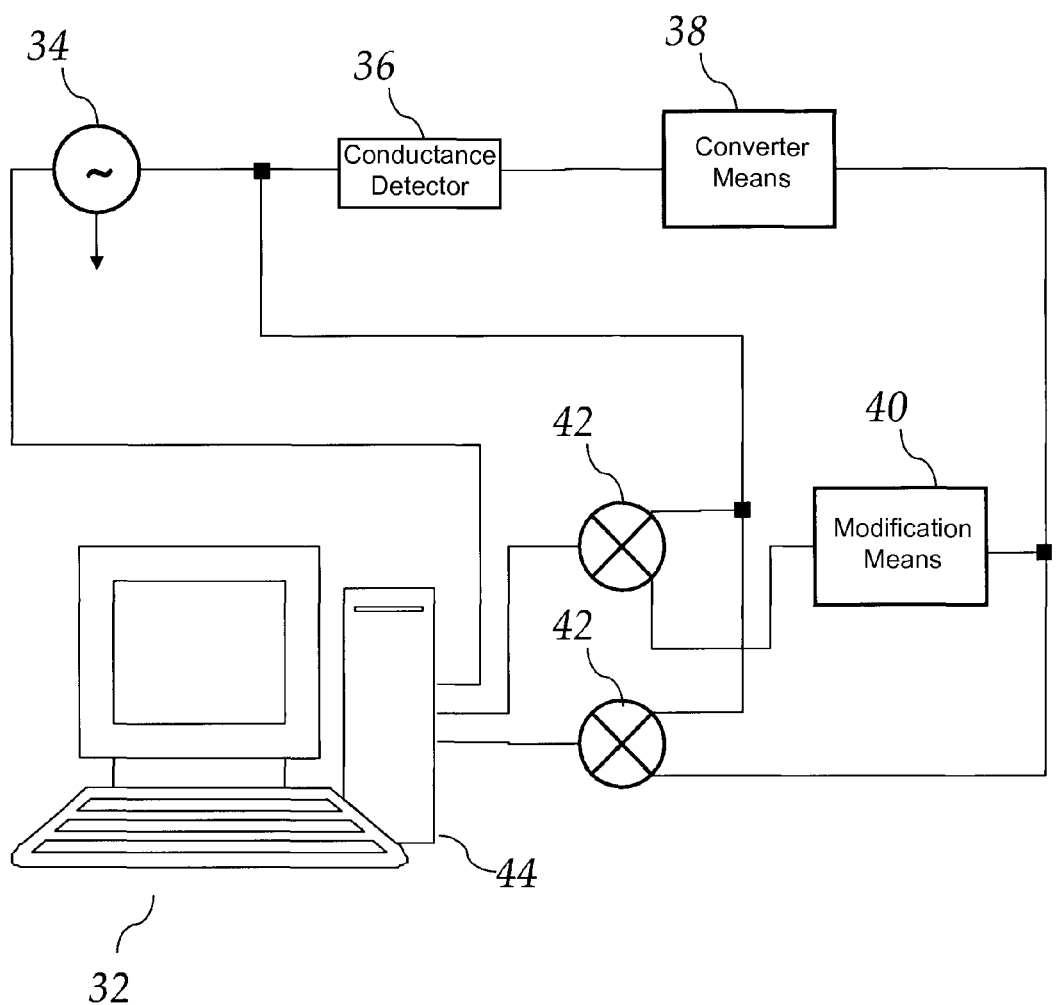
FIG. 3 is a schematic illustration of a data handling system and a circuit for use with a conductance detector in accordance with a preferred embodiment of the invention.

FIG. 3 is a schematic illustration of a detector system 32 in accordance with a preferred embodiment of the invention. Detector system 32 includes a data handling system 44. Data handling system 44 in a preferred embodiment of the invention includes means for inputting, storing, processing, displaying and transmitting data such as a microprocessor system such as a laptop or desktop computer. Other data handling systems will be obvious to those skilled in the arts and may include analog-to-digital converters, digital-to-analog converters as well as various types of means for data storage, display, processing, transmission (including wireless varieties), and the like.

Power supply 34 (also referred to as an electronic source) is configured for generating an electrical drive such as a current or voltage. Data handling system 44 (which includes a computer processor, and may include an operator interface, screen etc) may control, as a function of time, various parameters of the power supply 34. For example, if power supply 34 generates an electrical signal (current or voltage) that varies sinusoidally, data handling system 44 may control the amplitude, frequency, phase, as well as potentially time variation of any one or more of these parameters. Other time variations of the power supply 34, such as square wave, triangular wave, pseudo-random time dependence, etc. will be obvious to those skilled in the arts.

The electrical signal is applied to a conductance detector 36 (shown as item 20 in FIG. 2). In a preferred embodiment, a voltage is applied to the conductance detector, and a resulting response (current) is detected. Detector system 32 may include a signal detector. For example, it may include converter means 38 to convert the response of the conductance detector 36 into a form that is convenient for data handling system 44 to input. For example, if the response generated by conductance detector 36 is a current, converter means 38 may include electrical components such as resistors, op-amps, and the like to convert the current to a voltage which can be conveniently detected.

Detector system 32 may be configured to include modification means 40 and convolution means 42 for processing the response of the conductance detector 36. The response of the conductance detector may be phase shifted by modification means 40, multiplied by the electrical drive and integrated by convolution means 42 to determine an out-of-phase component of the response of the conductance detector and then input by data handling system 44. At sufficiently low frequencies where the response of the conductance detector is limited by the low conductances of capacitances, the out-of-phase component of the conductance detector is dominated by the capacitance of the conductance detector which limits the current and is related to the dielectric constant of species detected. Similarly, the response of the conductance detector 36 may be multiplied by the electrical drive and integrated by convolution means 42 to determine an in-phase component of the response of the conductance detector and then input by data handling system 44.

At sufficiently high frequencies where capacitances give rise to large conductances, the in-phase component of the conductance detector is dominated by the resistance of the conductance detector which limits the current and is related to the conductivity of species detected. It is advantageous to measure both the in-phase and out-of-phase components. For example, in hexane, a presence of a species is difficult to detect via changes it induces in conductivity since hexane is insulating. But, given a large geometrical amplification factor, the species may be easily detectable via changes it induces in dielectric constant. In methanol, for example, the presence of a species may induce changes in both dielectric constant and conductivity and influence both the in-phase and the out-of-phase components. Detection of both types of changes is greatly aided by large geometrical amplification factors.

In another embodiment of the invention, a phase sensitive detection scheme (for example, using a lock-in amplifier) may be used to achieve the preceding functionality. In yet another embodiment of the invention, convolution means 42 may rectify the output of the conductance detector 36, essentially multiplying the output of the conductance detector with itself and integrating. In still another embodiment of the invention, one or both of modification means 40 and convolution means 42 may be implemented via software after the output of conductance detector 36 has been digitized.

In a preferred embodiment of the invention, a known temporal variation of the electrical drive, which may vary, for example, as a sine wave, square wave, a pseudo-random function, or in some other fashion, is used to improve signal-to-noise. Ultimately, the electrical drive induces a signal component in the response of the conductance detector that varies in time in a fashion that is related to the time variation of the electrical drive. Knowledge that the electrical drive varies in time in a known manner and that the signal component of the output and the electrical drive must vary in time in a related manner can be used to improve signal-to-noise using methods and means well-known in the arts. For example, if the electrical drive varies sinusoidally at an angular frequency ω, the desired signal component may vary at angular frequency ω, 2ω, 3ω, etc. Other frequency components in the response can be attributed to noise. This is one example of a general approach whereby correlation methods and apparatus may be used to improve signal-to-noise, that is, by correlating the response of the conductance detector with the known temporal variation of the electrical drive and thereby rejecting noise. Such correlation methods and apparatus may employ Fourier transformation, lock-in techniques, wavelet analysis, Hadamard transforms, Shah convolution Fourier transform analysis (SCOFT), convolution methods, and the like that are generally well known in the noise reduction arts.

FIG. 4 provides schematic illustrations of different perspectives of a housing for a conductance detector in a preferred embodiment of the invention. The housing is preferably fashioned using materials that are chemically inert to species, mobile phases and the environment, are able to suitably withstand temperatures to which the housing may be subjected, are substantially leak proof, are portable, a suitably electrically insulating and may be conveniently machined or molded.

Examples of materials that may be used include polymers such as polytetrafluoroethylene and polyetheretherketone. The housing provides an enclosure for the conductance detector into which the mobile phase and sample mixture enter, interact with the conductance detector and exit. Therefore, the housing is preferably substantially leak-proof. Preferably, the housing is fashioned so that the conductance detector may be replaced and the housing reused. The housing also provides a means for bringing the electrical drive to and the response from the conductance detector in a substantially leak-proof manner.

It will be appreciated that while several different embodiments of the cell structure have been described and illustrated herein, the present invention is not to be limited to these particular embodiments. Rather, the key point of the present invention is the provision of a cell structure, through which the fluid containing the species being detected, configured to give a geometric amplification factor of about 1 meter, which is far in excess of anything commercially available at present. It will be appreciated that there are numerous different types of configurations that will satisfy this, but it is the realization that increasing the geometric amplification factor that gives a very extraordinary, and very surprising increase in sensitivity thereby allowing both changes in conductivity and dielectric constant due to the presence of the chemical and/or biological species. By biological species we mean biomolecules, cells, mitochondria etc.

Figure 4A:
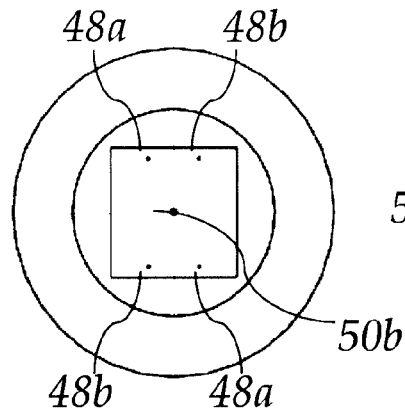
FIGS. 4a-c and d-f are illustrations providing different perspectives of an inlet and an outlet portion of a housing, respectively, for use with a conductance detector, FIGS. 4a, c, d and f are end views perpendicular to a cylindrical axis of the housing and FIGS. 4b and e are side views parallel to the cylindrical axis of the housing.
Figure 4D:
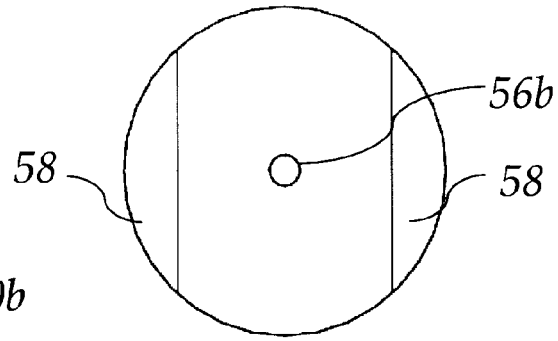
Figure 4B:
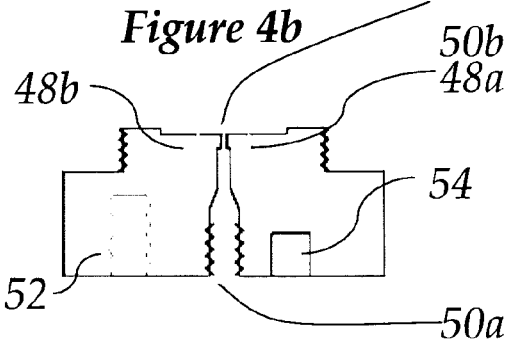
Figure 4E:
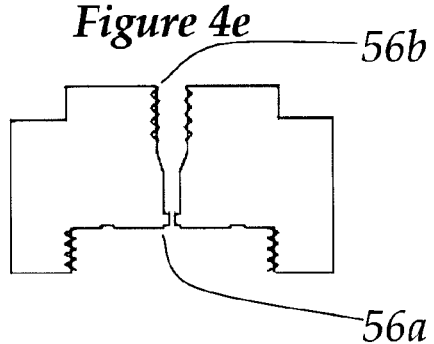
Figure 4C:
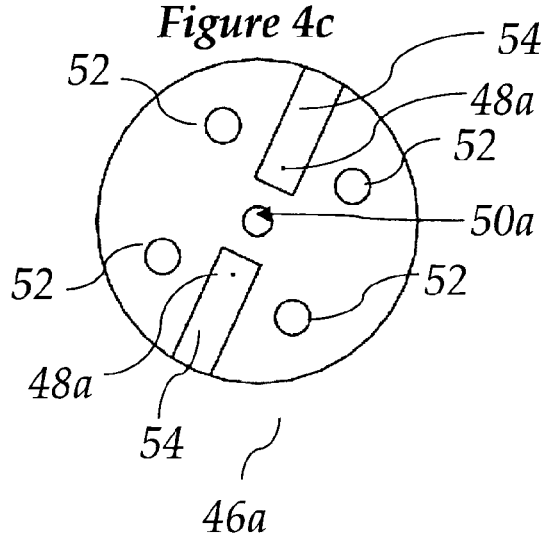
Figure 4F:
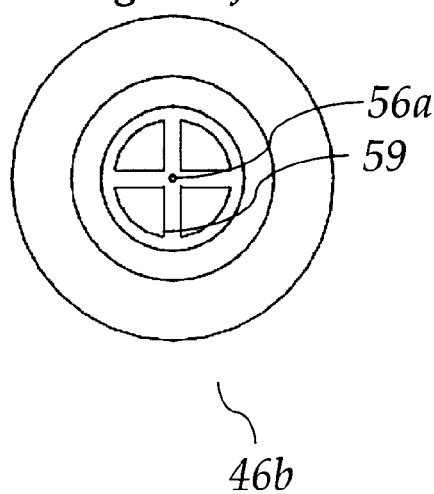

FIGS. 4a-c and d-f illustrate an inlet portion of the housing 46a and an outlet portion of the housing 46b, respectively. The inlet portion and the outlet portion may be secured to each other via a screw means, enabling facile access to the conductance detector and a leak-proof seal. Wires that, respectively, carry the electrical drive to and conductance detector response from the conductance detector pass through entrance holes 48a and exit holes 48b. Exit holes 48b are blind and serve to anchor wires, preventing them from sliding out of the housing. The wires are partially uninsulated and form a pair of conducting rails between entrance holes 48a and exit holes 48b on which first contact 23 and second contact 24 of the conductance detector rest. Outlet portion of the housing 46b screws onto inlet portion of the housing 46a, pressing the conductance detector against the wires and holding it in place. Entrance holes 48a and exit holes 48b may be provided with means to ensure the mobile phase and the sample mixture do not leak. For example, for liquid sample mixtures and mobile phase, the entrance holes 48a and exit holes 48b may be fashioned such that they are sufficiently small so as to substantially reduce or eliminate leaks.

If needed, a sealant may be used. Slots 54 may be provided to reduce the length of entrance holes 48a to facilitate their fabrication. The inlet portion of the housing 46a has a tapped aperture 50a that can accept a standard compression fitting for holding tubing through which mobile phase and a sample mixture flow to the conductance detector via a through aperture 50b. Similarly, outlet portion of the housing 46b has a tapped aperture 56b that can accept a standard compression fitting for holding tubing through which mobile phase and a sample mixture flow from the conductance detector via a through aperture 56a. The mobile phase and a sample mixture thus flow through aperture 50b onto the conductance detector to be detected, around the conductance detector and out of the housing through aperture 56a behind the conductance detector. Since the mobile phase surrounds the conductance detector, gradients in temperature and pressure that can undesirably change the geometrical factor of the detector are reduced. The housing preferably has a small dead volume to minimize peak broadening. Nevertheless, the housing may be provided with flow channels 59 to enable the mobile phase and sample mixture to flow easily so as not to make the internal pressure too high.

The housing may be provided with tapped holes 52 for securing the housing. For example, the housing may be secured in a box to which a connector may also be secured. Wires to and from the housing may be connected to the connector, so that electrical connections can be easily made using standard connectors and plugs. The housing may also be provided with slots 58 so that it may be gripped with tools to facilitate unscrewing apart or screwing together the inlet portion of the housing 46a and the outlet portion of the housing 46b.

Many variations of the housing shown in FIG. 4 are readily apparent. For example, in one preferred embodiment, a planar substrate with an inlet aperture may be affixed to the conductance detector, such as those illustrated in FIGS. 2h and 2i, causing a sample mixture to flow through flow paths to be sensed. This desirably lowers the conductance detector's dead volume and increase the sensitivity of the conductance detector by confining the liquid within the sensitive portion of the detector. The sample mixture may then exit the conductance detector from the sides or from an exit aperture in the planar substrate.

In another variation, the conductance detector with a planar substrate affixed causing a sample mixture to flow through flow paths may be housed in a housing to thermally stabilize the conductance detector. In yet another variation, the conductance detector may be fabricated so as to be an integral part a microfluidic platform so that the microfluidics platform forms the housing. Many such variations of the housing will be readily apparent to those skilled in the arts.

Figure 5:
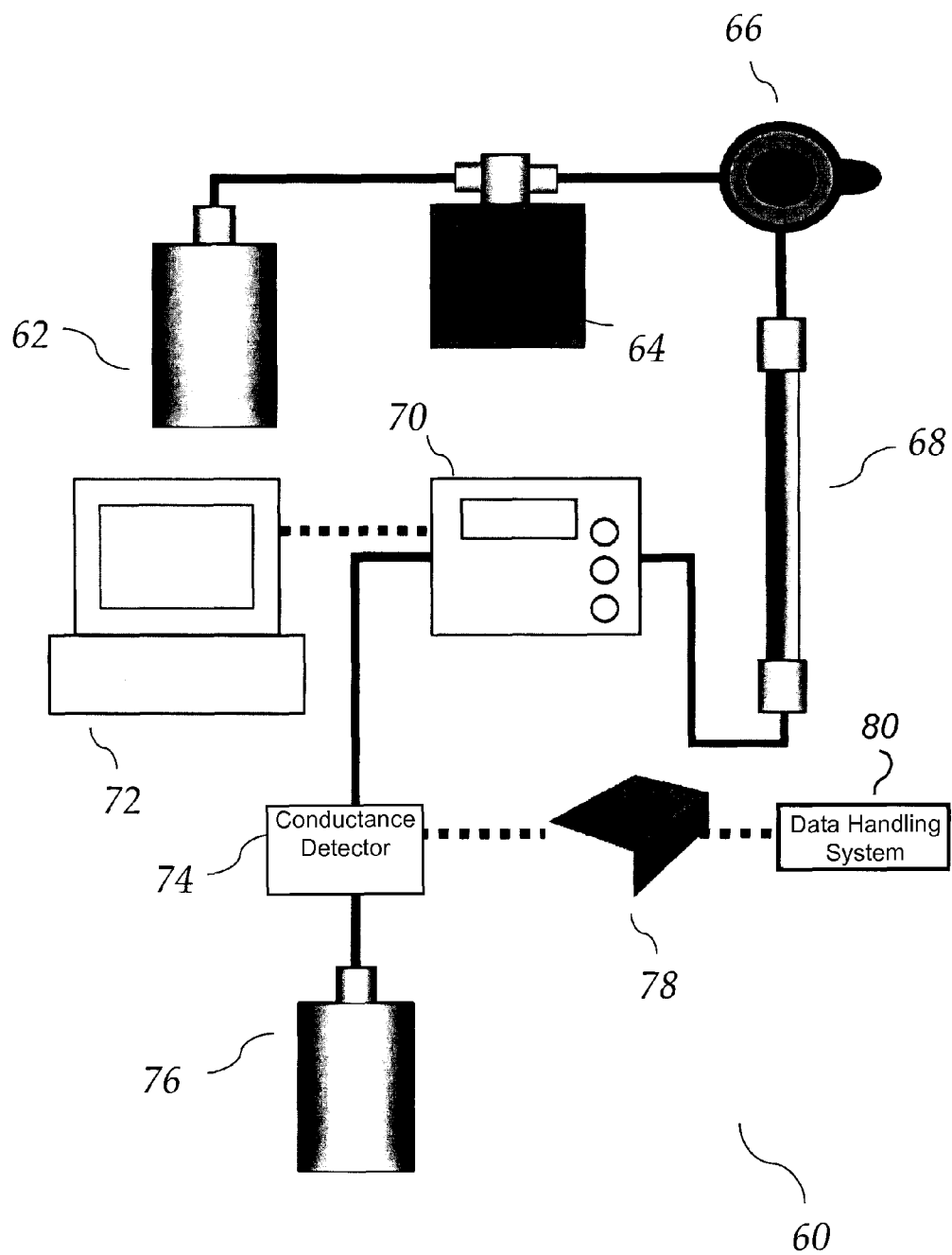
FIG. 5 is a schematic illustration of an HPLC system with a conductance detector incorporated in accordance with a preferred embodiment of the invention.
Figure 6A:
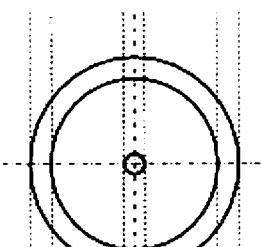
FIGS. 6a and b are schematic illustrations of a flash column adaptor for the housing for use with the conductance detector, FIGS. 6a and b are end and side views of the flash column adaptor, respectively.
Figure 6B:
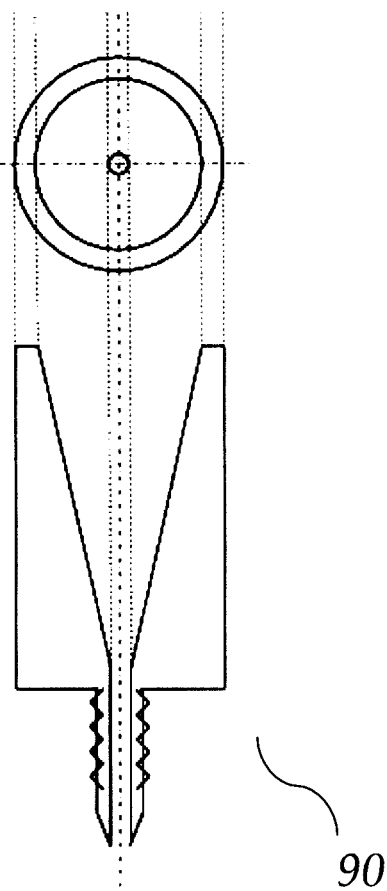
FIG. 6c through f are schematic illustrations of a flash column adaptor for the housing for use with the conductance detector.
Figure 6C:
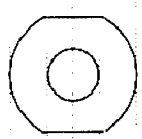
Figure 6D:
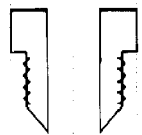
Figure 6E:
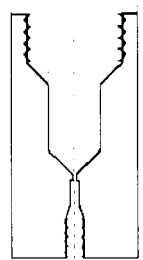
Figure 6F:
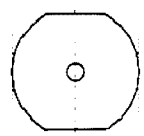

FIG. 5 is a schematically illustrates a separation apparatus 60, for example an HPLC system, with a conductance detector 74 incorporated in accordance with a preferred embodiment of the invention. Although an HPLC system is shown by way of example, it will be apparent to those skilled in the arts that the conductance detector 74 may be employed not just in HPLC systems but in a variety of separation apparatus as well, including apparatus employing gas mobile phases, electrophoresis, other liquid chromatography systems including those based on flash chromatography, etc. In separation apparatus 60 shown, pump 64 pumps mobile phase from reservoir 62 through column 68. A sample mixture is injected into the mobile phase via injector 66. Separation of the sample mixture into component species may be monitored using a standard detector 70, for example a UV-Vis detector.

HPLC systems typically employ a personal computer 72 to control the system and for data handling. After passing through the standard detector, the mobile phase and various species from the sample mixture are ejected into waste container 76. Conveniently, conductance detector 74 may be incorporated into separation apparatus 60 just before the waste. Thus, the conductance detector 74 can be easily incorporated into separation apparatus 60 in a modular fashion and does not alter its operation. Conductance detector 74 interfaces with electronics 78 which in turn interfaces with data handling system 80. Data handling system 80 may or may not include personal computer 72.

Figure 7:
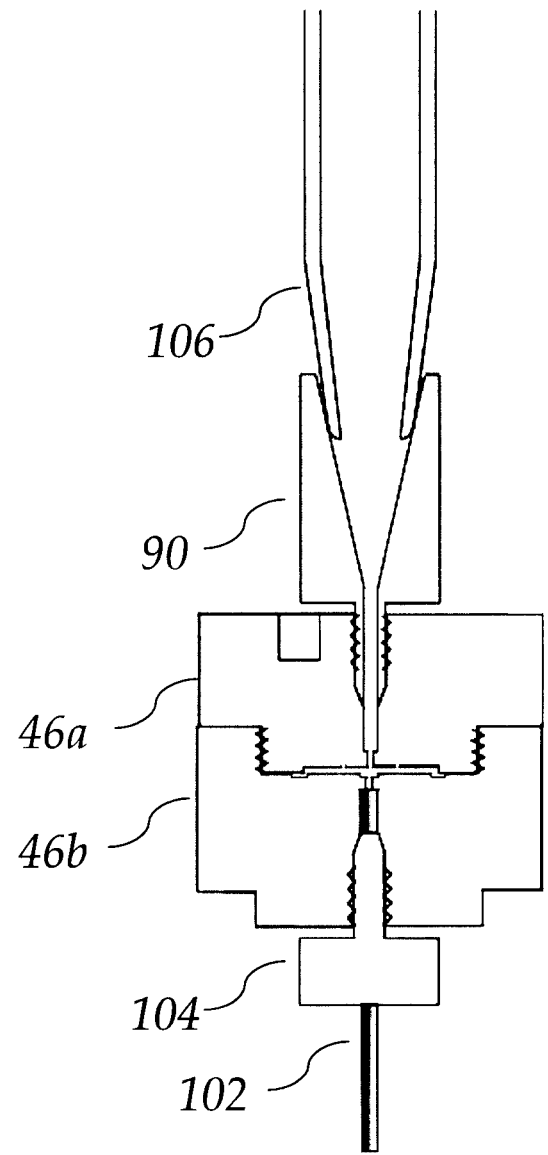
FIG. 7 is a schematic illustration showing the flash column adaptor shown in FIGS. 6a and b, the conductance detector and the housing in an assembled configuration.

FIGS. 6 and 7 illustrate that the conductance detector may be used, not just with an HPLC system, but with a variety of separation apparatus. FIGS. 6a and 6b schematically illustrate end and side views of flash adaptor 90, respectively. Flash adaptor 90 has a tapered opening that can mate with a flash column and a tapped protrusion that can thread into a tapped hole in inlet portion of the housing 46a for the conductance detector.

FIGS. 6c through 6f schematically illustrate various views of flash adaptor 91. Flash adapter 91 functions as a union of compression fittings. A first end of flash adapter 91 has a compression fitting that mates with a flash column. A second end of flash adapter 91 has a compression fitting that connects to inlet portion of the housing 46a via a tube and compression fittings.

FIG. 7 schematically illustrates how flash adaptor 90, for example, and conductance detector may be used in a flash chromatography system. Instead of flash adapter 90, flash adapter 91, may be used with the aid of a pair of standard compression fittings and tubing. Mobile phase and components of sample mixture flow through flash column 106, flash adaptor 90, inlet portion of the housing 46a, outlet portion of the housing 46b, compression fitting 104 and then tubing 102 whence they may be collected. Species are detected as they flow past the conductance detector housed by the inlet and outlet portions of the housing (46a and 46b, respectively).

Figure 8:
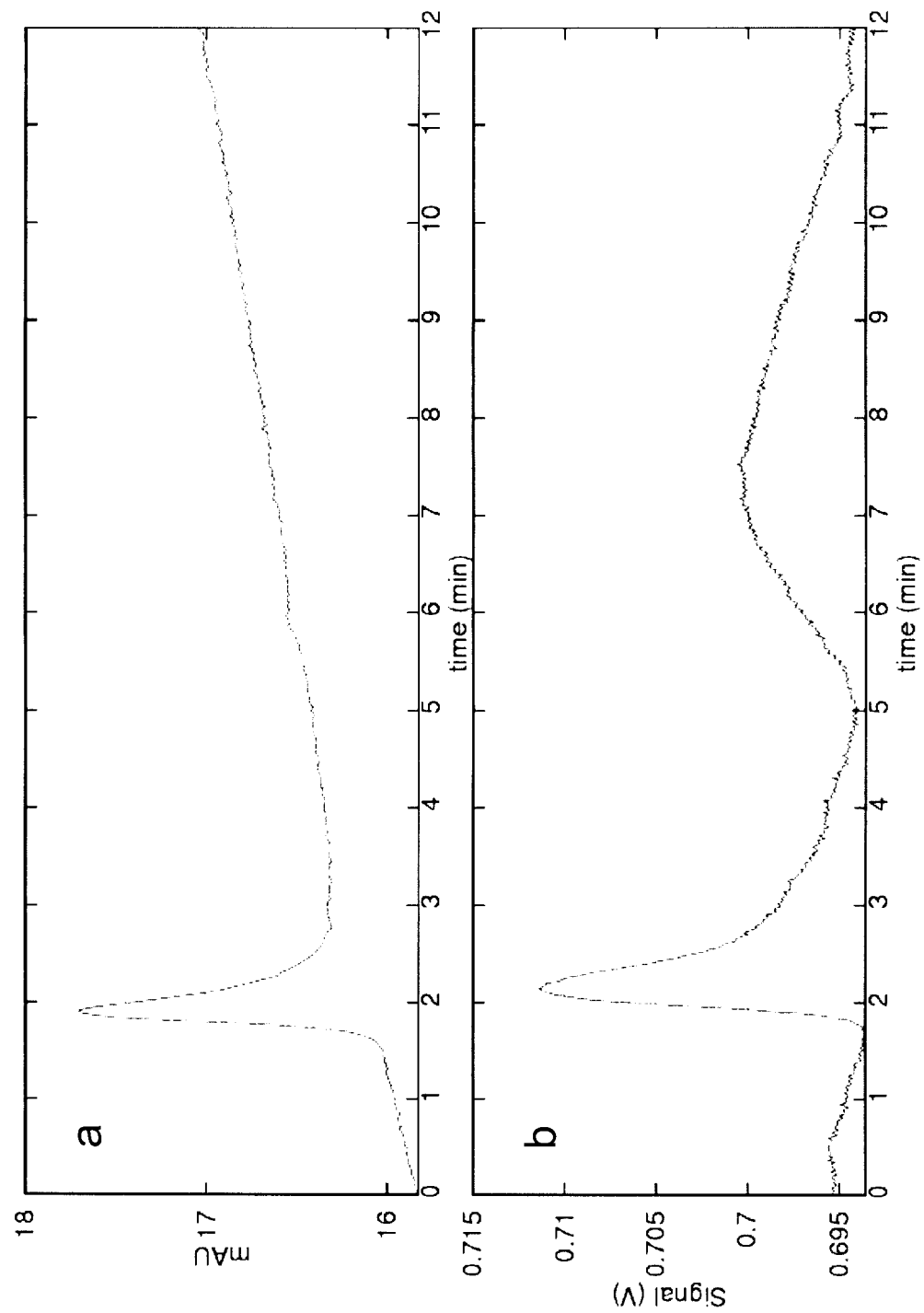
FIGS. 8a and b show HPLC data obtained simultaneously using a UV-Vis and a conductance detector, respectively. Acetyl salicylic acid (50 µL, 10 µM) with an unknown contaminant was injected in the HPLC as the sample mixture.

FIGS. 8a and 8b display data obtained using an HPLC with a UV-Vis and a conductance detector, respectively. The conductance detector employed is as illustrated in FIG. 2, the detector system as in FIG. 3, the housing as in FIG. 4 and the separation apparatus as in FIG. 5. Electronic source 34 is a voltage source oscillating sinusoidally at 1 kHz, 90 $mV_{p-p}$. The time dependent voltages should be kept below redox thresholds in case detection of redox current is not desired. Data shown in FIG. 8b were obtained using detector system 32, employing modification means 40, in particular a phase shifter, and convertor means 38, in particular a current-to-voltage convertor. Thus, the voltage data in FIG. 8b are proportional to the out-of-phase component of the response of the conductance detector and depend on $G_\in$, amplified by a geometrical amplification factor, acetyl salicylic acid (ASA, 50 µL, 10 µM) and an unknown contaminant were injected in the HPLC as the sample mixture.

Peaks in both FIGS. 8a and 8b appear at approximately 2 minutes due to the ASA. The peak can be attributed to ASA since varying concentration results in varying peak height as discussed below. The ASA peak in FIG. 8a appears earlier than in FIG. 8b because the UV-Vis detector is located before the conductance detector. The $G_\in$ data in FIG. 8b also shows a broad peak that extends from approximately 5 minutes to 12 minutes. This peak is not evident in the UV-Vis data in FIG. 8a, except perhaps as a small, narrow peak at approximately 6 minutes. Evidently, the sample mixture used for this measurement contains at least one species that does not have a strong UV-Vis absorbance. Being able to detect such contaminations easily using HPLC is desirable, illustrating a utility of the present invention.

A conductance detector according to preceding embodiments of the invention may be advantageously used for monitoring column conditioning. Simply waiting for a period of time to ensure column conditioning, as commonly practiced in the art, is undesirable. If one waits too long, resources are wasted. If one waits too little, data obtained can be compromised.

Monitoring column conditioning using UV-Vis is more difficult than using the conductance detector since many contaminants may not have significant UV-Vis absorbance. Also, initially when a separation apparatus with a column is started, the column is likely more contaminated than it is after mobile phase has passed for a period of time. Typically, the UV-Vis detector is turned on during this initial period, after having been turned off to prolong UV-Vis lamp life. As the UV-Vis lamp equilibrates after being turned on, the UV-Vis signal varies significantly, making monitoring column conditioning using the UV-Vis detector more challenging.

Figure 9:
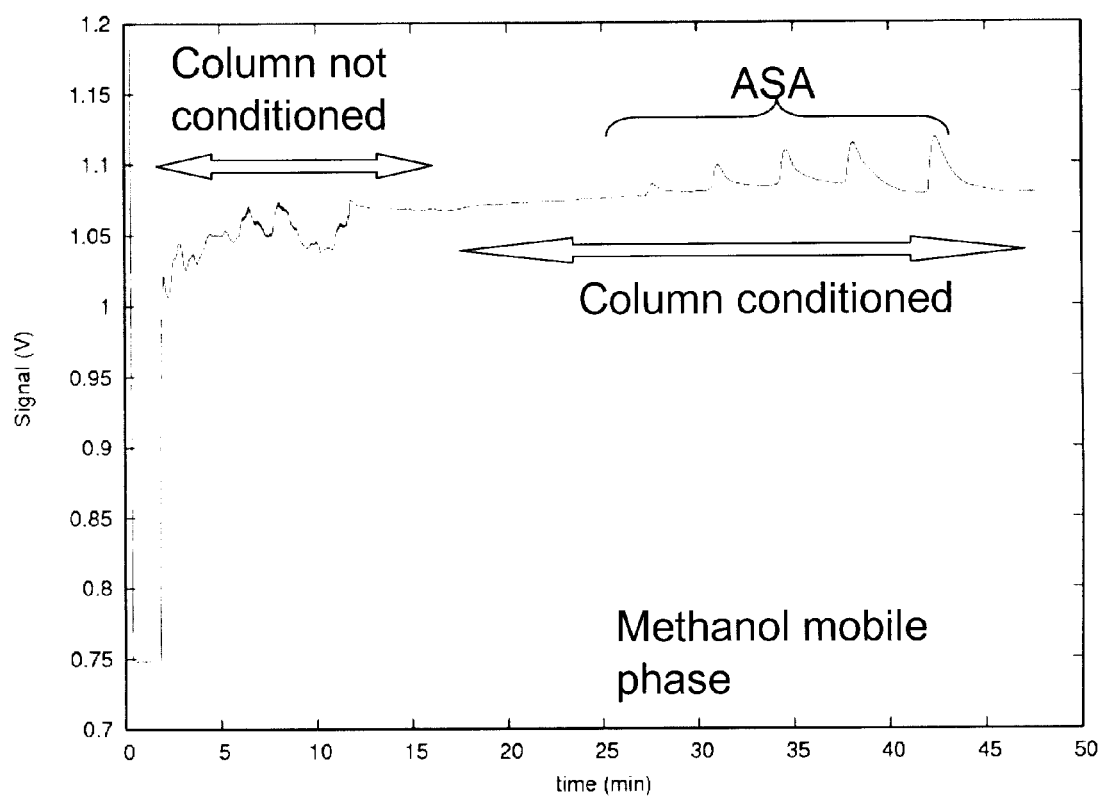
FIG. 9 shows HPLC data obtained using the conductance detector both before and after the HPLC column is conditioned. After the column was conditioned, samples with acetyl salicylic acid were injected into the HPLC. Volumes of all injections were 50 µL and acetyl salicylic acid concentrations were 10, 25, 50, 75 and 100 µM.

The use of a conductance detector for monitoring column conditioning is demonstrated in FIG. 9. Data shown in FIG. 9 were obtained using an HPLC system (with a conductance detector as described in the context of FIG. 8) and with methanol as the mobile phase. The data exhibit a great deal of noise for the first 15 minutes due to contamination, likely primarily from the column. After 15 minutes, the data are much quieter, and the column is said to be "conditioned". Subsequently, ASA samples with increasing concentrations were injected, and peaks with correspondingly increasing heights can be observed in FIG. 9. Clearly, with respect to FIG. 9, if the ASA sample had been injected when the column was not conditioned, the corresponding peaks would have exhibited much poorer signal-to-noise.

FIG. 10 illustrates yet another utility of the present invention, namely that it may be employed even if the composition of mobile phase is varied. Varying composition of the mobile phase is a procedure commonly employed to aid in separation of sample mixtures and is referred to as gradient elution. It is noteworthy that refractive index detectors are unable to function using gradient elution since the refractive index of the mobile phase changes, potentially by a large amount, with its composition, making detection of smaller changes in refractive index due to species in the sample mixture difficult to detect. FIGS. 10a and b show HPLC data obtained simultaneously using a UV-Vis detector and conductance detector, respectively. The mobile phase was composed of methanol and acetonitrile, and the fraction of methanol was varied from 100% to 0% (from 5 minutes to 15 minutes) and from 100% to 0% (from 25 minutes to 35 minutes). The changing mobile phase gives rise to a changing background in data from both types of detectors. In the UV-Vis data, the background changes linearly and symmetrically as the fraction of methanol was varied linearly from 100% to 0% and back to 100%. In the conductance data, the background changes asymmetrically. As the concentration of methanol decreases from 100%, the background changes slowly initially reflecting an affinity of the conductance detector's surface for methanol. Similarly, as the concentration increases from 0%, the background changes rapidly initially as methanol accumulates on the conductance detector's surface. These data confirm an ability of the conductance detector to function as a sensor. As the composition was varied, ASA (50 µL, 10 µM) was injected, both as the fraction of methanol was increasing and decreasing (at approximately, 12 minutes and 32 minutes, respectively).

Importantly, in both the UV-Vis and conductance data, the background changes fall well within the range of both detectors. Further, notwithstanding this sufficiently wide range of the detectors, the conductance data have high resolution and low noise, and peaks due to species injected are resolvable even in the unprocessed conductance data. Visualization of the peaks due to the species injected may be aided by mitigating effects of the changing background due to the mobile phase. The mitigation may be performed using different procedures well known in the arts. For example, one can employ a reference conductance detector that detects just the mobile phase without the sample mixture to aid in the mitigation since the reference conductance detector can monitor the changing background. Alternatively, the effect of the changing background may be mitigated numerically using techniques well known in the arts. For example, the data may be differentiated numerically to emphasis rapid changes caused by species from a sample mixture. The changing background may be fit to various functions such as polynomials, ratios of polynomials, exponentials, etc. and then its influence can be mitigated. The changing background may be filtered using high pass filters, Fourier filters, etc. to emphasis rapid changes caused by species from a sample mixture.

It will be appreciated by those skilled in the art that embodiments of the invention may be employed with a variety of separation methods and apparatus including, but not restricted to, those related to various forms of chromatography (with liquid and/or gas mobile phases, with various stationary phases that are disposed in columns, capillaries, microchannels or substantially planar substrates, including chromatography such as flash, ion, thin layer, normal phase, reverse phase, size exclusion, affinity, supercritical fluid, chiral, counter current, fast protein liquid chromatography, multi-dimensional chromatography, HPLC, ultrahigh performance chromatography, etc.), electrophoresis (gel, capillary, or microchannel), 2D electrophoresis, isotachophoresis, etc.

Although separation methods and apparatus are important applications for embodiments of the present invention, it is to be understood that the embodiments disclosed herein may be adapted to a wide range of uses. In one embodiment, conductance detections systems and methods may suitably functionalized for use in sensor (including biosensor) applications. In another non-limiting example, embodiments of the invention may be used to assess a degree of contamination of a liquid or gas sample, e.g. water, solvent, chemical product, and the like. In yet another non-limiting example, embodiments of the invention may be used to assess the cleanliness of a container by adding a clean solvent to the container, immersing the conductance detector and comparing the conductance of the solvent in the container with that of the clean solvent.

While preceding embodiments of the invention have been disclosed within the context of sensors for measuring $G_\in$ and/or $G_o$ conductance via the detection of a displacement and/or external current, those skilled in the art will appreciate that embodiments of the invention may be further adapted for use in electrochemical detection methods and apparatus (with or without the inclusion of a reference electrode). For example, a voltage ramp can be generated using a data acquisition card or a voltage supply and applied to the conductance detector, and the current can be measured. Alternatively, by summing a slowly varying electrical signal (e.g. a voltage ramp) with a rapidly varying sinusoidal electrical signal using a summing amplifier and applying the summed signal to conductance detector, the conductance can be measured at various voltages. In general, a power supply can have a plurality of generators that generate a plurality of electrical signals with a plurality of time dependencies that (in combination or by direct application to the conductance detector) can generate a plurality of time dependent responses. Furthermore, with the aid of suitable functionalization using chemical/and or biological functionalities, they can be used as a basis for electrochemical sensor methods and apparatus. The electrochemical detection methods and apparatus or electrochemical sensor methods and apparatus may be used in separation methods and other sensing applications, as noted above.

Figure 11A:
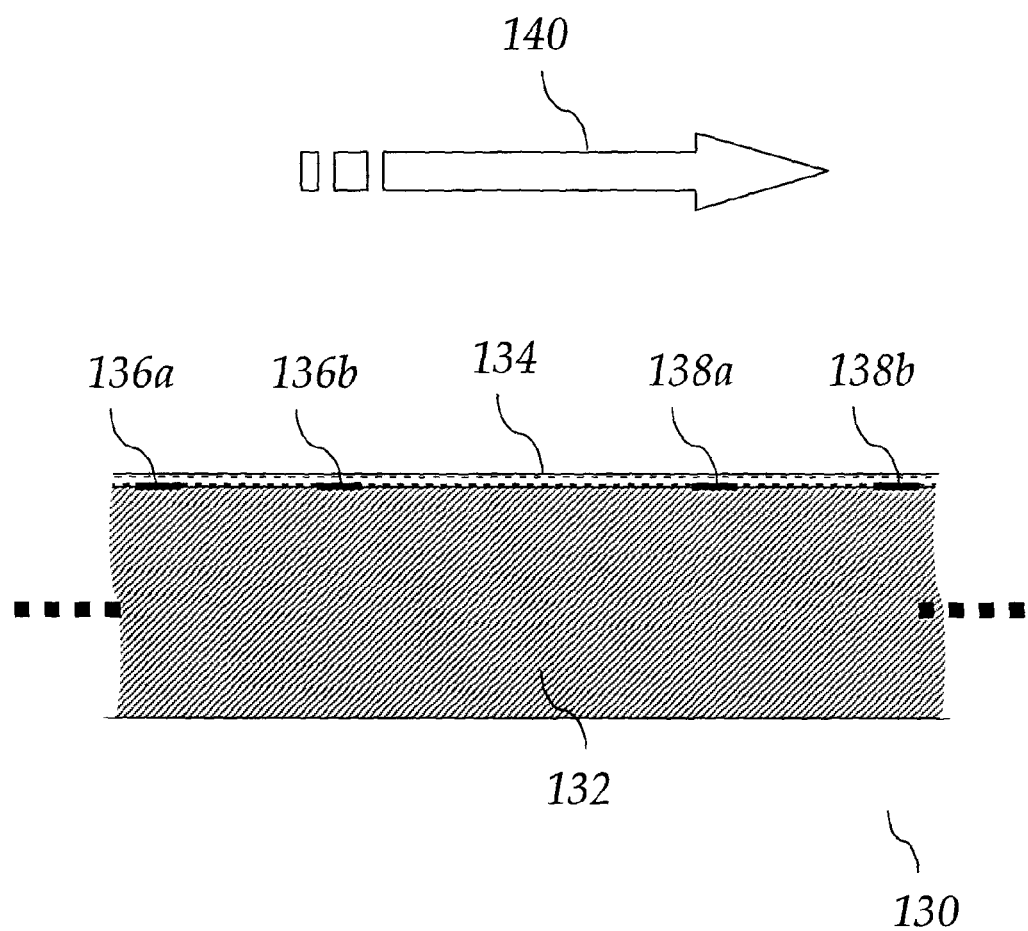
FIG. 11a shows a schematic illustration of a conductance detector in accordance with another preferred embodiment of the invention.
Figure 11B:
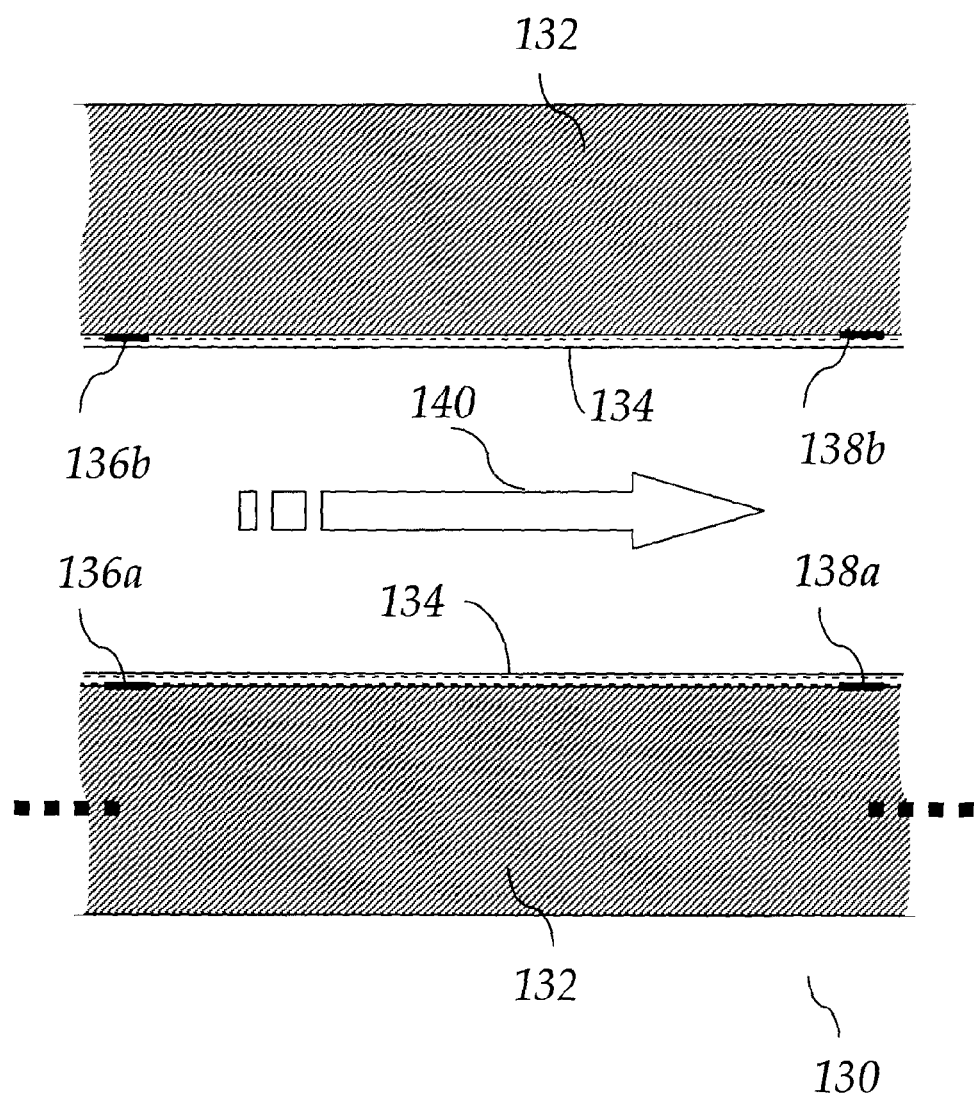
FIG. 11b shows a schematic illustration of a conductance detector in accordance with another preferred embodiment of the invention.

FIGS. 11a and 11b show schematic illustrations of conductance detector 130 in accordance with yet other embodiments of the present invention. Conductance detector 130 has an array of electrodes comprising one or more electrode pairs. In FIGS. 11a and 11b, 136a and 136b comprise one electrode pair, and 138a and 138b comprise another. Electrodes in each electrode pair are held rigidly with respect to each other by rigid architecture 132 in the embodiment shown in FIG. 11a.

In the embodiment shown in FIG. 11b, electrodes in each electrode pair may be held rigidly with respect to each other by affixing rigid architectures 132 rigidly with respect to each other if necessary. Rigid architecture 132 may be planar or columnar and may comprise an insulating material such as, but not limited to, glass, silicon, silica, polymer, quartz, alumina, a printed circuit board, and the like. Conductance detector 130 may be fashioned using a variety of processes and materials well known in the electronics arts, including those such as lithography that as used to fabricate circuit elements on silicon wafers and printed circuit boards.

One or both of each electrode in a given electrode pair may be electrically insulated by insulation 134 to significantly reduce external current from flowing through the array or electrodes. Insulation 134 may additionally or alternatively serve to protect the array of electrodes chemically. Insulation 134 also serves to prevent the potential of any electrodes from detrimentally influencing separation of species in the sample mixture 140 being sensed by the conductance detector. Insulation 134 may be fashioned using materials and methods well known in the electronics arts; for example, it may be fashioned by spin coating resist, by depositing insulation via thermal deposition, sputtering, CVD, etc., by spontaneously oxidizing a surface, etc.

The electrical drive or plurality of electrical drives applied to the conductance detector may be time dependent, varying in time slowly so that the conductance detector substantially probes permittivity, varying rapidly so that the conductance detector substantially probes conductivity, or varying at some intermediate rate so that the conductance detector probes some parallel/series combination of resistance and capacitance. In a preferred embodiment of the invention, the geometrical amplification factors are sufficiently large so that the conductance sensed by the conductance detector is significant (that is, at least one hundredth as large) compared with the background conductance of the rest of the circuit.

As discussed above, the geometrical amplification factor, which is key to the present invention may be made sufficiently large by increasing the area sensed by the conductance detector. Geometrical amplification factors may also be made sufficiently large by having a plurality of electrode pairs. If the plurality of electrode pairs are distributed such that they all sense the sample mixture at substantially the same point in the separation process (as in FIG. 2, for example), signals from the various electrode pairs may be summed, thereby effectively increasing the conductance detector's area, geometrical amplification factors and signal-to-noise.

In some applications, it may be preferable to have electrode pairs at different points along a separation process. In general, the electrode pairs need not be similar to each other in terms of their size and/or shape, and they need not be periodically disposed with respect to each other. For example, in one embodiment, there may be a higher density of electrode pairs near the beginning of a separation process and fewer at the end, etc. If the electrode pairs are distributed at various different locations such that they sense the sample mixture at different points in the separation process, then signals from the various electrode pairs may be combined through display (e.g. plot as a multi-dimensional plot) and/or processed then combined, thereby still effectively increasing the conductance detector's area, geometrical amplification factor and signal-to-noise as discussed further below.

This approach for increasing geometrical amplification factors is compatible with a desire to keep the cross sectional area of a sample mixture small in certain separation apparatus, for example, in capillary and microchannel electrophoresis. Geometrical amplification factors may also be made sufficiently large by sufficiently reducing the distance between electrodes within electrode pairs. This consideration must be counterbalanced by the teachings of FIG. 1 and the related discussion that, as the distance between electrodes is reduced, the conductance detector senses a smaller region and may sense only a small portion of the sample mixture or perhaps none of the sample mixture. It is desirable to have sample mixture 140 pass as close as possible to the electrode pairs and to have insulation 134 as thin as possible while maintaining its insulating nature. It is further desirable to have the distance between the electrodes no less than one tenth the scale of the smallest distance between sample mixture 140 and electrode pairs in order for the electrode pairs to sense sample mixture 140.

In one embodiment of the invention, conductance detector 130 may have chemical and/or biological recognition elements disposed thereon to aid in a separation or detection of species in a sample mixture. For example, if a sample mixture includes a hydrophobic species, interaction between the hydrophobic species and conductance detector 130 may be enhanced by functionalizing conductance detector 130 with a hydrophobic functionality (such as an alkane). If a sample mixture includes an antibody species, interaction between the antibody species and conductance detector 130 may be enhanced by functionalizing conductance detector 130 with a complementary antigen species. Many such functionalizations and combinations of functionalizations with various functionalities to modify interactions between a species in a mixture and a surface are well known in the arts and may be employed with the present invention.

In another embodiment of the invention, a stationary phase may be disposed on conductance detector 130 in a proximity of at least one electrode pair. For example, if conductance detector 130 is employed with gel electrophoresis, the stationary phase may comprise a material such as agarose, starch, alginate, carrageenin or polyacrylic polymer gel. If conductance detector 130 is employed with thin layer chromatography, then the stationary phase may comprise silica particles. Many such examples will be evident to those skilled in the arts.

Conductance detector 130 may be used as part of a detector system that is similar to detector system 32 schematically illustrated in FIG. 3. In order to accommodate one or more electrode pairs, one or more multiplexers may be employed to apply the electrical drive generated by electronic source 34 to various electrode pairs. In order to reduce the effects of stray fields, preferably when the electrical drive is applied to an electrode pairs and in case conductance detector 130 comprises a plurality of electrode pairs, all remaining electrode pairs may be left electrically floating to reduce detrimental effects of stray couplings.

Figure 12:
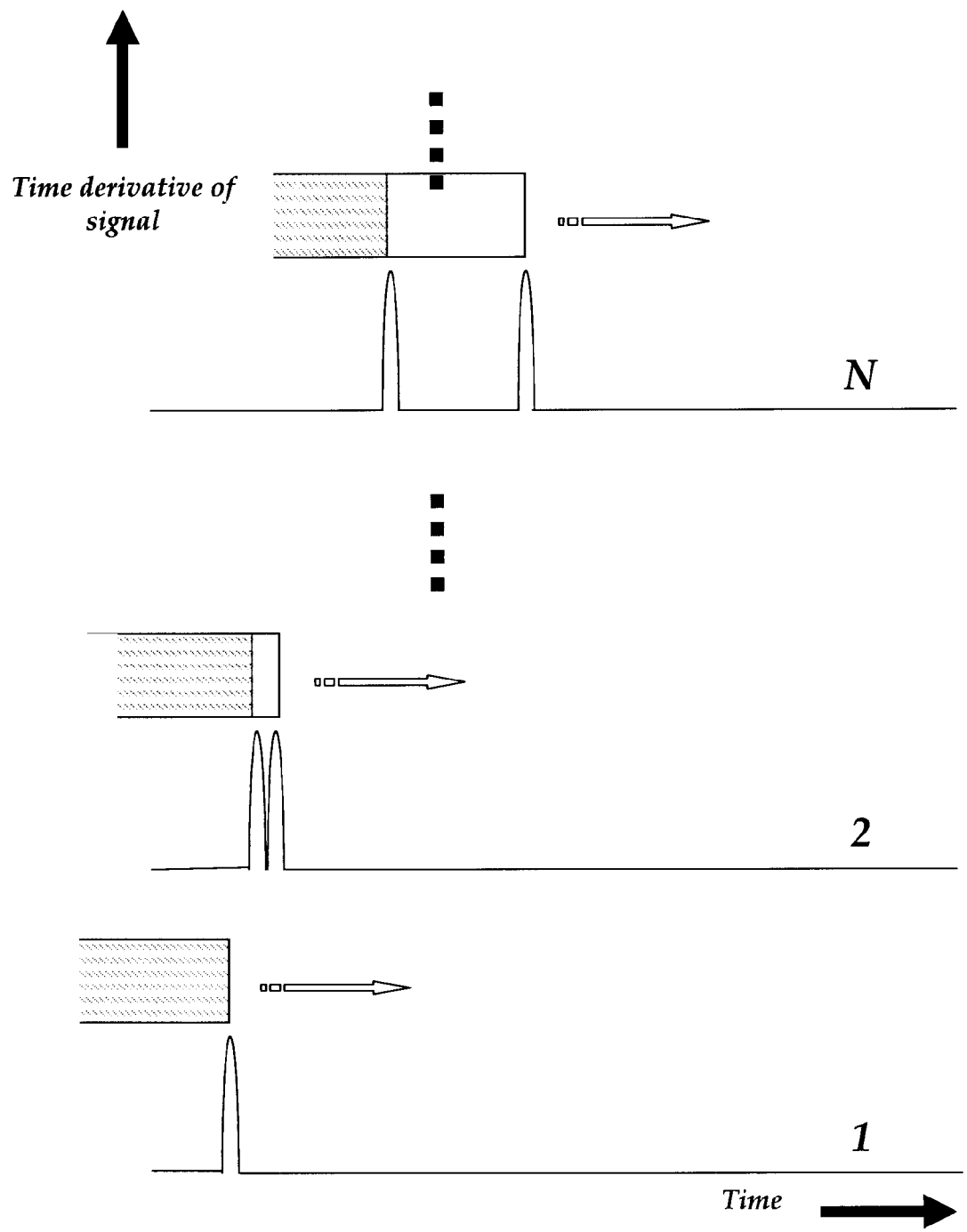
FIG. 12 shows signals from conductance detectors positioned at various locations along a separation apparatus in which two species are separated.

In the arrangement of electrode pairs shown in FIG. 11, for example, reducing the distance between electrodes also has a desirable effect of providing information about species in the sample mixture before the species are actually completely separated from each other. FIG. 12 illustrates the progression of a separation process using a sample mixture containing two species. The sample mixture is illustrated at various points during a separation process, labeled 1, 2, . . . N . . . , respectively, as monitored by electrode pairs of a conductance detector located various points along a separation apparatus.

As the separation process progresses, the front edges of the two species separate further apart with respect to each other. The time derivative of the signal of the electrode pairs will display peaks that correspond to the front edges of the species in the sample mixture. The peaks will separate as the front edges of the species separate, even if the spatial distribution of the species overlap significantly as shown in FIG. 12.

As the distance between electrodes decreases, the resolution of the peaks increases and it becomes possible to obtain information about the species in a time that is much shorter than the time required to separate the species completely. This is very desirable for a number of reasons. The separation may be monitored as it proceeds, and information about the species in the sample mixture can be obtained. This is in contrast to methods and apparatus commonly used (for example gel electrophoresis amongst others) where the separation is observed only after the separation has progressed for potentially a significant period of time and after species are rendered optically detectable. The separation may be aborted early (potentially leading to considerable saving of resources such as time, cost, etc.) or, if further separation is desired, the separation may be allowed to proceed, possibly with adjusted separation parameters in order to improve the separation.

An additional benefit of this aspect of the invention is that data obtained corresponding to points 1, 2, . . . N . . . may be plot as a multi-dimensional plot. They may also be processed to account for the fact that they were obtained at different points along the separation process and then combined to yield improved signal-to-noise. By way of example, peaks in data obtained as a function of time at point 1 along the separation process may be processed such that the peaks are overlapped with corresponding peaks in data obtained as a function of time at point 2, etc. Data obtained at points 1, 2, . . . N . . . , after such processing, may then be summed. This combining or processing and then combining has the effect of essentially increasing the geometrical amplification factor of the conductance detector. It will be apparent to those skilled in the arts that, although the embodiment of the invention shown in FIG. 12 relates to a 1-dimensional separation process, the invention can be readily applied to higher dimensional separation processes.

Figure 13:
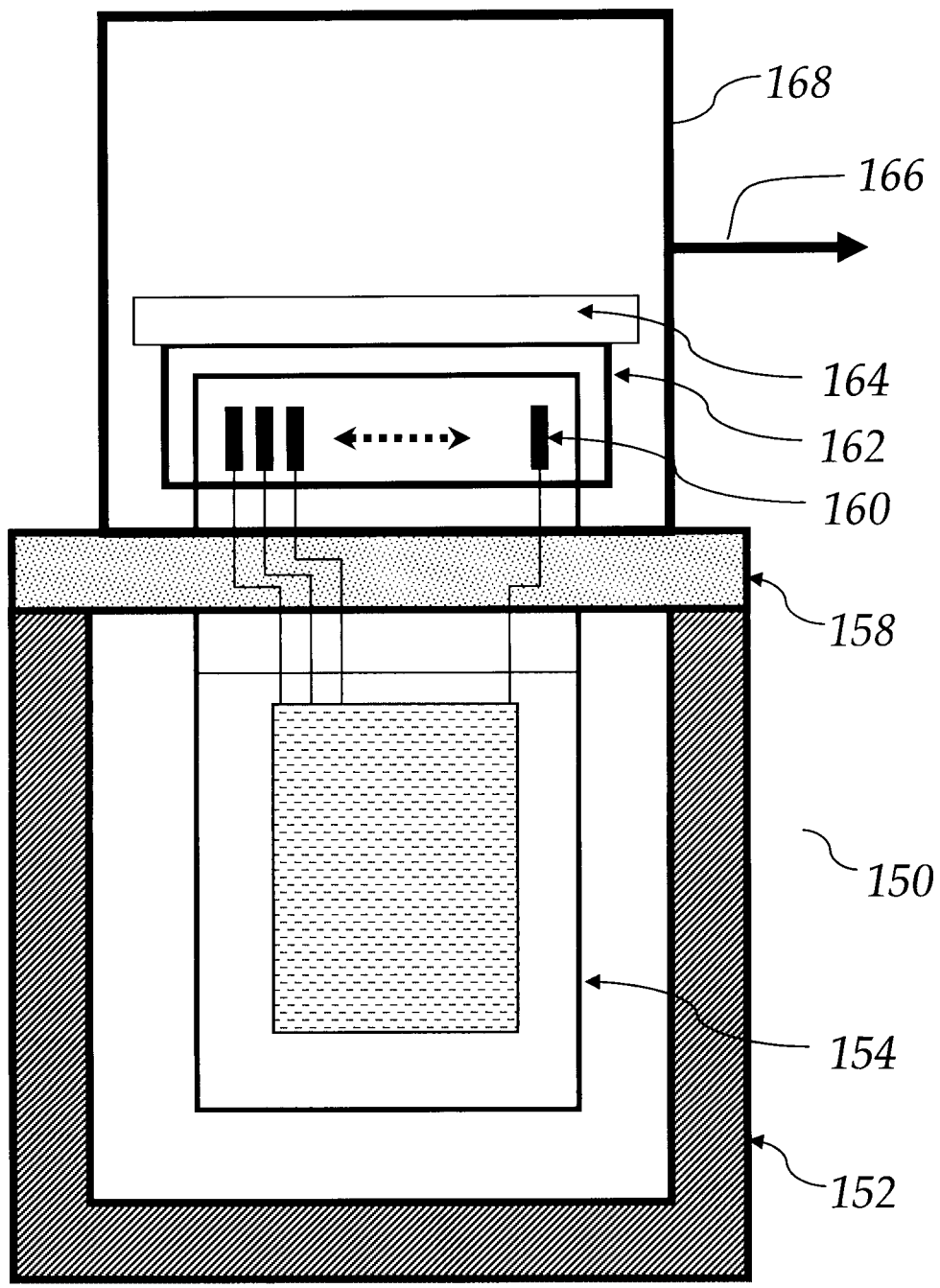
FIG. 13 shows a schematic illustration of a separation apparatus with a conductance detector in accordance with another preferred embodiment of the invention.

FIG. 13 illustrates another embodiment of this invention as applied to a separation apparatus 150 with substantially planar conductance detector 154. By way of example, the separation apparatus may function by chromatography (for example thin layer chromatography), electrophoresis (for example planar gel electrophoresis), and the like. Container 152 contains a mobile phase and may be covered with a cover 158. Conductance detector 154 comprises a rigid architecture (including a substrate), insulator and one or a plurality of electrode pairs. Conductance detector 154 may be fashioned using a variety of processes and materials well known in the electronics arts, including those relating to fabrication of circuit elements on substrates such as silicon wafers, glass, silica, alumina, printed circuit boards, acetate, kapton, plastic, etc.

The one or a plurality of electrode pairs is/are electrically connected to an array of contact pads 160, which may in turn be contacted to circuitry on circuit board 164 via connector 162. As a result, conductance detector 154 may be easily removed and replaced. The circuitry may interface with additional electronics via interface 166 and is enclosed in box 168. Separation apparatus 150 may be used with a detector system that is similar to detector system 32 schematically illustrated in FIG. 3. In order to accommodate one or a plurality of electrode pairs, one or more multiplexers may be employed to apply the electrical drive generated by electronic source 34 to various electrode pairs. In order to reduce the effects of stray couplings, preferably when the drive is applied to an electrode unit cell and in case separation apparatus 150 comprises a plurality of electrode pairs, all remaining electrode pairs are left floating.

Figure 14:
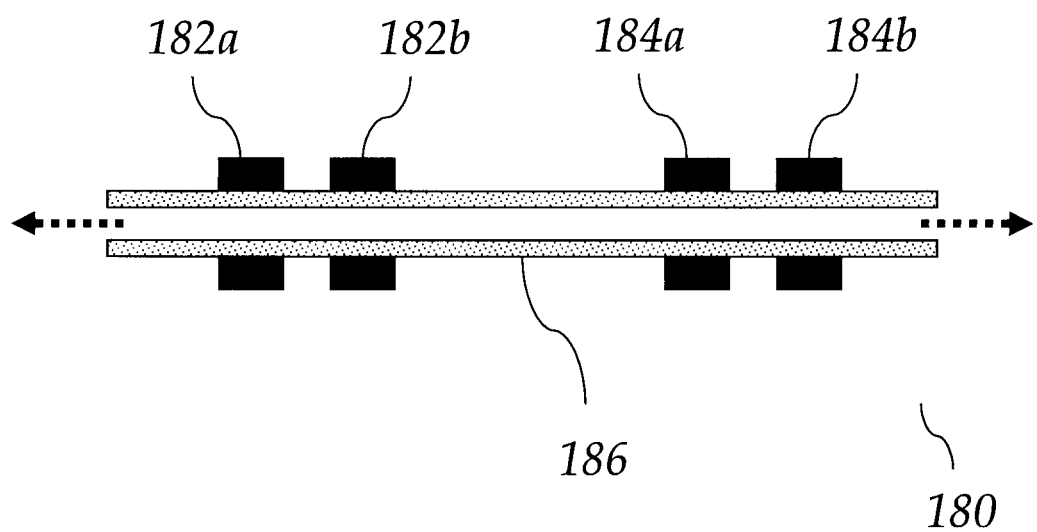
FIG. 14 shows a schematic illustration of a conductance detector in accordance with another embodiment of the invention.

FIG. 14 illustrates yet another embodiment of the present invention relating to a separation apparatus that is based on a substantially columnar, capillary or microchannel separation. Conductance detector 180 comprises one or a plurality of electrode pairs. In FIG. 14, electrodes 182*a* and 182*b* comprise one electrode pairs, and electrodes 184*a* and 184*b* comprise another. Electrodes in each electrode pairs are held rigidly with respect to each other by rigid architecture 186, which may comprise glass, silicon, silica, polymer, quartz, alumina and the like. The one or a plurality of electrode pairs is/are preferably insulated to prevent the electrode unit cell(s) from detrimentally influencing separation of species in the sample mixture being sensed by the conductance detector. Conductance detector 180 may be used with a detector system that is similar to detector system 32 schematically illustrated in FIG. 3. In order to accommodate one or a plurality of electrode pairs, one or more multiplexers may be employed to apply the electrical drive generated by electronic source 34 to various electrode pairs.

It will be readily apparent to those skilled in the arts that the conductance detection system and method disclosed herein have many applications. Selected embodiments involve monitoring a species as it flows, in which case a housing with an inlet and an outlet is preferred, as previously described.

Figure 15:
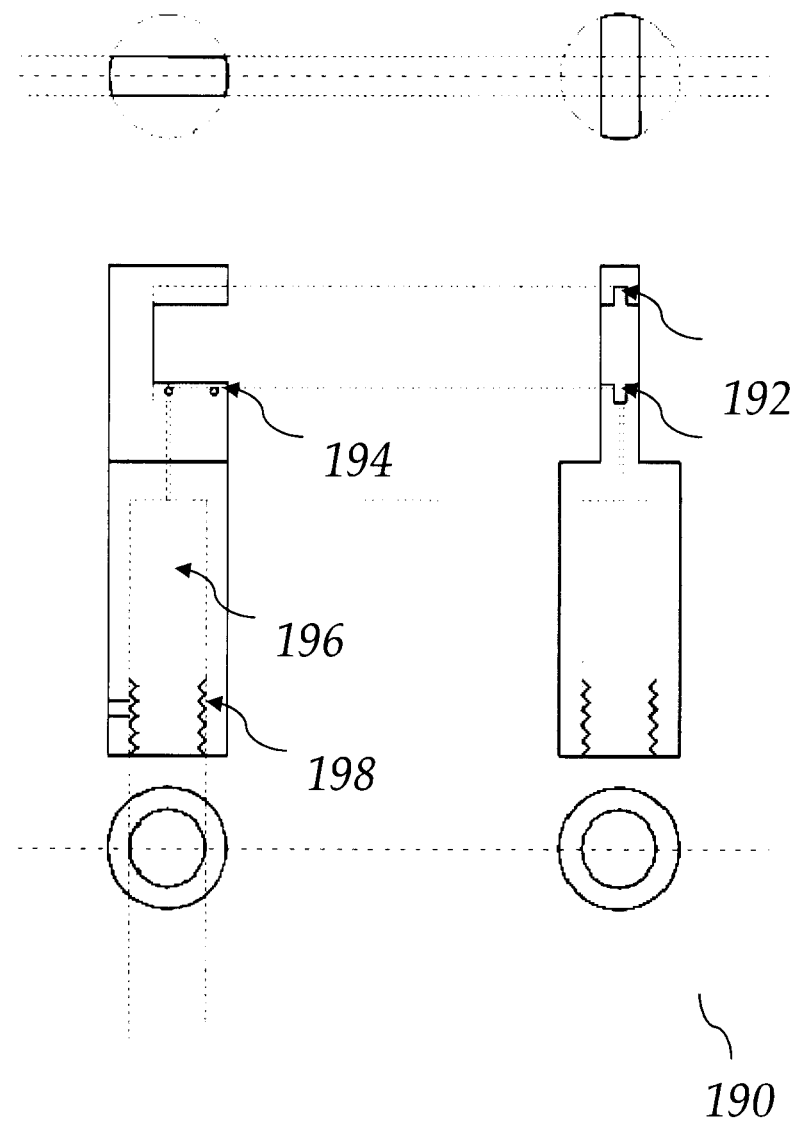
FIG. 15 shows schematic illustrations of a housing for a conductance detector in accordance with another preferred embodiment of the invention. Various perspectives of the housing are shown.

Other embodiments involve exposure of the conductance detector to volume that may contain a species, for example, by immersing the conductance detector into a vessel containing a liquid. Exemplary yet non-limiting embodiments include assessing the purity of a medium (gas or liquid), the cleanliness of a container, the quality of a product, and sensing the presence of a biomolecule in a mixture. For such applications, one may employ holders that advantageously facilitate exposure of the conductance detector to the species. FIG. 15 shows one example of such a holder. Holder 190 contains holding means 192, such as slots, in which a conductance detector may be held using springs, clips, or the like. Wires for carrying signals to or from the conductance detector may pass through holes 194 and cavity 196. Holder 190 also has accommodation means 198 to accommodate electrical contacts for the wires; accommodation means 198 may comprise a tapped hole to accommodate a BNC connector, holes to accommodate pins, etc.

As used herein, the terms "comprises" and "comprising" are to be construed as being inclusive and open rather than exclusive. Specifically, when used in this specification including the claims, the terms "comprises" and "comprising" and variations thereof mean that the specified features, steps or components are included. The terms are not to be interpreted to exclude the presence of other features, steps or components.

It will be appreciated that the above description related to the invention by way of example only. Many variations on the invention will be obvious to those skilled in the art and such obvious variations are within the scope of the invention as described herein whether or not expressly described.

REFERENCES CITED

U.S. Patent Documents

| U.S. Pat. No. | Issued | Inventor |
|---|---|---|
| 4,814,690 | March 1989 | Melcher et al. |
| 5,045,798 | September 1991 | Hendrick |
| 6,242,264 B1 | June 2001 | Natan et al. |
| 6,458,327 B1 | October 2002 | Vossmeyer |
| 6,824,974 B2 | November 2004 | Pisharody et al. |
| 6,764,583 B2 | July 2004 | Miles |
| 4,920,047 | April 1990 | Giaever et al. |
| 6,773,926 B1 | August 2004 | Freund et al. |
| 4,301,401 | November 1981 | Roof et al. |
| 6,995,348 B2 | February 2006 | Bradley et al. |
| 5,852,495 | December 1998 | Parce |
| 6,489,785 B2 | December 2002 | McAllister |
| 6,491,805 B1 | December 2002 | Gordon et al. |
| 6,441,625 B1 | August 2002 | McAllister et al. |
| 6,632,400 | October 2003 | Brennen et al. |
| 6,159,353 | December 2000 | West et al. |
| 5,194,133 | March 1993 | Clark et al. |
| 6,045,676 | April 2000 | Mathies et al. |
| 5,949,899 | September 1999 | Ng |
| 5,410,412 | April 1995 | Gombocz et al. |
| 5,100,529 | March 1992 | Fujii |
| 4,930,893 | June 1990 | Manian |
| 4,728,882 | March 1988 | Stanbro |
| 4,822,566 | April 1989 | Newman |
| 5,846,708 | December 1998 | Hollis et al. |
| 6,846,639 B2 | January 2005 | Miles et al. |
| 6,764,583 B2 | July 2004 | Miles |
| 6,824,974 B2 | November 2004 | Pisharody et al. |

| U.S. Patent Publication | Published | Inventor |
|---|---|---|
| 0238112 A1 | October 2007 | Sohn et al. |
| 0192653 A1 | December 2002 | Stetter et al. |
| 0227373 A1 | October 2005 | Flandre et al. |

OTHER PUBLICATIONS

Roy et al. "Mass produced nanogap sensor arrays for ultrasensitive detection of DNA" JACS (2009) 131, 12211-12217.

Yi et al. "Theoretical and experimental study towards a nanogap dielectric biosensor" Biosensors and bioelectronics (2005) 20, 1320-1326.

Hu et al. "The integration of gold nanoparticles with semiconductive oligomer layer for development of capacitive immunosensor" Sensors and Actuators B (2005) 106, 641-647.

Benningfield et al "A commercially available dielectric constant detector for liquid chromatography and its application" J. Chromatog. Sci. (1981) 19, 115-123.

Poppe et al. "Construction of a permittivity detector for liquid chromatography" J. Chromatog. Sci. (1972) 10, 16A.

Haderka "Role of mobile phase permittivity in the use of the capacitance detectors in liquid chromatography" J. Chromatog. (1970) 52, 213-220.

Haderka "Use of the resonance principle in the permittivity detectors for liquid chromatography" J. Chromatog. (1970) 54, 357-366.

Haderka "The prospects of selective detection by capacitance detectors in liquid chromatography" J. Chromatog. (1971) 57, 181-191.

Fuller et al. "On-Line Process Liquid Exclusion Chromatography Applied to the Production of Styrene-Butadiene Copolymers" J. Chromatog. Sci. (1979) 17, 661-665.

Stelzle et al. "Sensitive detection of protein adsorption to supported lipid bilayers by frequency-dependent capacitance measurements and microelectrophoresis" Biochimica et Biophysica Acta. (1989) 981, 135-142.

Wohltjen et al. "Colloidal Metal-Insulator-Metal Ensemble Chemiresistor Sensor" Anal. Chem. (1998) 70, 2856-2859.

Joseph et al. "Self-Assembled Gold Nanoparticle/Alkanedithiol Films: Preparation, Electron Microscopy, XPS-Analysis, Charge Transport, and Vapor-Sensing Properties" J. Phys. Chem. B (2003) 107, 7406-7413.

Joseph et al. "Chemiresistor coating from Pt- and Au-nanoparticle/nonanedithiol films: sensitivity to gases and solvent vapors" Sensors and Actuators B (2004) 98, 188-195.

Su et al. "Miniaturized Chemical Multiplexed Sensor Array" J. Am. Chem. Soc. (2003) 125, 9930-9931.

Leopold et al. "Growth, conductivity, and vapor response properties of metal ion-carboxylate linked nanoparticle films" Faraday Discuss. (2004) 125, 63-76.

Joseph et al. "Gold-nanoparticle/organic linker films: self-assembly, electronic and structural characterisation, composition and vapour sensitivity" Faraday Discuss. (2004) 125, 77-97.

Kuban et al "Fundamental aspects of contactless conductivity detection for capillary electrophoresis. Part I: Frequency behavior and cell geometry" Electrophoresis (2004) 25, 3387-3397.

Kuban et al "Fundamental aspects of contactless conductivity detection for capillary electrophoresis. Part II: Signal-to-noise ratio and stray capacitance" Electrophoresis (2004) 25, 3398-3405.

Matysik "Advances in amperometric and conductometric detection in capillary and chip-based electrophoresis" Microchim Acta (2008) 160, 1-14.

Kuban et al. "A review of the recent achievements in capacitively coupled contactless conductivity detection" Analytica Chimica Acta (2008) 607, 15-29.

Pumera "Contactless conductivity detection for microfluidics: Designs and applications" Talanta (2007) 74, 358-364.

Tay et al. "Floating resistivity detector for microchip electrophoresis" Electrophoresis (2007) 28, 4620-4628.

Fu et al. "Fabrication and testing of high-performance detection sensor for capillary electrophoresis microchips" Biomed Microdevices (2008) 10, 73-80.

Kuban et al. "High-performance liquid chromatography with contactless conductivity detection for the determination of peptides and proteins using a monolithic capillary column" J. of Chromatography A (2007) 185-191.

Takeuchi et al "Use of a capacitance measurement device for surrogate noncontact conductance measurement" Talanta (2008) 617-620.

Wang et al "Movable contactless-conductivity detector for microchip capillary electrophoresis" Anal. Chem. (2003) 4475-4479.

Tanyanyiwa et al "High-voltage capacitively coupled contactless conductivity detection for microchip capillary electrophoresis" Anal. Chem. (2002) 74, 6378.

Nadherna et al "Properties of the contactless impedance detector with insulated wire electrodes placed inside the flowing liquid stream" Electroanalysis (2007) 19, 2413-2418.

Kwok et al. "Shah convolution differentiation Fourier transform for rear analysis in microchip capillary electrophoresis" J. of Chromatography A (2001) 924, 177-186.

Kaneta "Hadamard transform CE" Anal. Chem. (2001) 73, 540A-547A.

Eijkel et al. "Wavelet transform for Shah convolution velocity measurements of single particles and solutes in a microfluidic chip" Lab on a Chip (2001) 1, 122-126.

Kwok et al. "Characterisation of Shah convolution Fourier transform detection" Analyst (2001) 126, 1640-1644.

McReynolds et al. "Shah and sine convolution Fourier transform detection for microchannel electrophoresis with a charge coupled device" Anal. Chem. (2002) 74, 5063.

McReynolds et al. "Comparison of Hadamard transform and signal-averaged detection for microchannel electrophoresis" Anal. Chem. (2004) 76, 3214-3221.

Crabtree et al. "Shah convolution Fourier transform detection" Anal. Chem. (1999) 71, 2130-2138.

Therefore what is claimed is:

1. A conductance detector for detecting conductivity and/or dielectric constant of one or more chemical and/or biological species in a phase, comprising:
a cell structure including
a rigid architecture having a top surface a portion of which is electrically conductive forming a first conductive component;
a second conductive component substantially overlapping the first conductive component and spaced from said first conductive component by an insulating component;
one or more flow pathways between the first conductive component and the second conductive component for the chemical and/or biological species to flow;
the first conductive component, the second conductive component and the insulating component having an architecture selected to give
a cross sectional area over which a displacement current and/or external current flows that is on an order of about 1 cm$^2$; and
a distance over which the displacement current and/or external current flows that is in a range from about nanometer to hundreds of microns and even higher;
a power supply for generating a time dependent electrical signal for inducing a time dependent response, the power supply being coupled to at least one of said first and second conductive components;
a signal detector coupled to at least one of said first and second conductive components for measuring the time dependent response; and
a microprocessor connected to said signal detector for determining changes in conductance caused by a presence of said chemical and/or biological species in said phase.

2. The conductance detector according to claim 1 wherein said signal detector is configured to measure one or both of a first component of the first time-dependent response that is an in-phase component related to a change in a sigma conductance and a second component that is an out of phase component related to a change in an epsilon conductance due to the presence of said chemical and/or biological species in said phase.

3. The conductance detector according to claims 1, wherein said power supply includes a generator for generating a plurality of time dependent signals with a plurality of time dependencies, and said power supply is configured to combine the plurality of time-dependent signals and to induce a time-dependent response with a plurality of time dependences.

4. The conductance detector according to claim 1, wherein the rigid architecture comprises a substrate fashioned from any one of silicon, glass, silica, alumina, a printed circuit board, acetate, kapton and plastic.

5. The conductance detector according to claim 1 wherein a flow surface of at least one of said flow pathways of the conductance detector is functionalized with a chemical and/or biological functionality that interacts with said chemical and/or biological species in said phase, wherein said flow surface, the first conductive component and the second conductive component are in close proximity to render significant any change in said sigma conductance and/or said change in said epsilon conductance due to said presence of said chemical and/or biological species.

6. The conductance detector according to claim 1 wherein the cell structure is replaceably housed in a housing or is housed in a microfluidics platform.

7. The conductance detector according to claim 1 wherein the phase being tested for the presence of the chemical and/or biological species is conveyed to the cell structure by a tube or by an adaptor.

8. The conductance detector according to claim 1 wherein the signal detector or the microprocessor are programmed to apply at least one correlation method to improve signal-to-noise of the conductance detector.

9. The conductance detector according to claim 8 wherein the correlation method includes one of Fourier transformation, lock-in techniques, wavelet analysis, Hadamard transforms, Shah convolution Fourier transform analysis or convolution methods.

10. The conductance detector according to claim 1 connected to a chromatography sample output of a chromatography apparatus to detect any chemical and/or biological species present in the chromatography sample output from said chromatography apparatus by said change in said sigma conductance and/or said change in said epsilon conductance caused by the presence of said chemical and/or biological species in said phase.

11. The conductance detector according to claim 10 wherein the chromatography apparatus is a gas chromatography apparatus, a thin layer chromatography apparatus, a high performance liquid chromatography apparatus, an ultra-high performance liquid chromatography apparatus, or a flash chromatography apparatus.

12. The conductance detector according to claim 1 connected to an electrophoresis sample output of an electrophoresis apparatus to detect said chemical and/or biological species present in the electrophoresis sample output from said electrophoresis apparatus by said change in said sigma conductance and/or said change in said epsilon conductance caused by the presence of said chemical and/or biological species in said phase.

13. The conductance detector according to claim 12 wherein the electrophoresis apparatus is a gel apparatus, a capillary apparatus or a microchannel electrophoresis apparatus.

14. The conductance detector according to claim 1 wherein the cell structure includes a plurality of cavities located in the insulating component into which the phase being tested for the presence of the chemical and/or biological species can enter as the phase flows through the cell structure.

15. The conductance detector according to claim 1 wherein said time dependent response is processed using a time-domain analysis technique including any one or combination of fourier transform, wavelet analysis, differentiation, and high pass filtering to emphasize contributions to said time-dependent response due to said chemical and/or biological species relative to contributions to said time-dependent response due to a changing composition of said phase.

16. The conductance detector according to claim 1 wherein the insulating component is fashioned by spin coating, deposition, or spontaneous oxidation.

17. A conductance detector for detecting conductivity and/or dielectric constant of one or more chemical and/or biological species dispersed in a phase and separated by an integrated substantially planar gel electrophoresis apparatus, comprising:
 a first rigid architecture having a top surface a portion of which is electrically conductive forming a first conductive component, the first component being insulated from the phase;
 a second conductive component, the second component being insulated from the phase;
 a gel component through which displacement current generated by the first or second conductive components flows;
 flow pathways through the gel component for the chemical and/or biological species to flow;
 a power supply for generating a time dependent electrical signal for inducing a time dependent response, the power supply being coupled to at least one of said first and second conductive components;
 a signal detector coupled to at least one of said first and second conductive components for measuring the time dependent response; and
 a processor connected to said signal detector configured to determine changes in conductance caused by a presence of said chemical and/or biological species.

18. The conductance detector according to claim 17 wherein the first and second conductive components comprise a plurality of electrode pairs disposed at different locations along the substantially planar gel electrophoresis apparatus such that
 the power supply and signal detector are coupled to each of the electrode pairs; and
 said processor and said signal detector configured to determine changes in conductance caused by a presence of said chemical and/or biological species in said phase in a proximity of each electrode pair.

19. The conductance detector according to claim 18 wherein
 a first and a second electrode from each pair are disposed on the first rigid architecture and a second rigid architecture, respectively, such that they substantially overlap;
 the first and second rigid architecture are spaced by a spacer; and
 the gel component, through which the phase containing the chemical and/or biological species to be separated flows, is disposed between the first and second rigid architecture.

20. The conductance detector according to claim 19 wherein the first and second rigid architectures are fashioned from silicon, glass, silica, alumina, a printed circuit board, acetate, kapton, or plastic.

21. The conductance detector according to claim 18, wherein the power supply and signal detector are coupled to each of the electrode pairs using multiplexers.

22. A method for detecting conductivity and/or dielectric constant of one or more chemical and/or biological species in a phase, comprising:
 flowing a phase being tested for the one or more chemical and/or biological species through a cell structure, the cell structure including
  a rigid architecture having a first electrically conductive component separated from a second conductive component by an insulating component,
  one or more flow pathways between the first conductive component and the second conductive component for the chemical and/or biological species to flow,
  the first conductive component, the second conductive component and the insulating component having an architecture selected to give
   a cross sectional area over which a displacement current and/or external current flows that is on an order of about 1 $cm^2$; and
   a distance over which the displacement current and/or external current flows that is in a range from about nanometer to hundreds of microns and even higher;
 applying a time dependent electrical signal to at least one of said first and second conductive components for inducing a time dependent response; and
 measuring the time dependent response and determining from said time dependent response any changes in conductance caused by a presence of said chemical and/or biological species in said phase.

23. The method according to claim 22 wherein said cell structure comprises said a rigid architecture having a top surface a portion of which is electrically conductive forming said first conductive component, and wherein said second conductive component substantially overlapps the first conductive component and spaced from the first conductive component by the insulating component.

24. The method according to claim 22 wherein said time dependent response is measured by a signal detector is configured to measure one or both of a first component of the first time-dependent response that is an in-phase component related to a change in a sigma conductance and a second component that is an out of phase component related to a change in an epsilon conductance due to the presence of said chemical and/or biological species in said phase.

25. The method according to claim 22 wherein said time dependent electrical signal is applied using a power supply which includes a generator for generating and combining a plurality of time dependent signals with a plurality of time dependencies, and said power supply is configured to combine the plurality of time-dependent signals and to induce a time-dependent response with a plurality of time dependences.

26. The method according to claim 22 wherein the rigid architecture comprises a substrate fashioned from any one of silicon, glass, silica, alumina, a printed circuit board, acetate, kapton and plastic.

27. The method according to claim 22 wherein a flow surface of at least one of said flow pathways of the conductance detector is functionalized with a chemical and/or biological functionality that interacts with said chemical and/or biological species in said phase, wherein said flow surface, the first conductive component and the second conductive component are in close proximity to render significant any change in said sigma conductance and/or said change in said epsilon conductance due to said presence of said chemical and/or biological species.

28. A method for detecting conductivity and/or dielectric constant of one or more chemical and/or biological species dispersed in a phase and separated by an integrated substantially planar gel electrophoresis apparatus, comprising:
 flowing said phase containing the one or more chemical and/or biological species through a substantially planar electrophoresis gel component which is located between a first electrically conductive component, the first electrically component being insulated from the phase and a second electrically conductive component, the second electrically component being insulated from the phase;

a gel component through which displacement current generated by the first or second conductive components flows;

flow pathways through the gel component for the chemical and/or biological species to flow;

applying a time dependent electrical signal for inducing a time dependent response at least one of said first and second conductive components wherein a displacement current is generated by the first or second conductive components flows;

measuring the time dependent response and processing the measured time dependent response for determining changes in conductance caused by a presence of said chemical and/or biological species in said phase.

29. The method according to claim 28 wherein the first and second conductive components comprise a plurality of electrode pairs disposed at different locations along the substantially planar gel electrophoresis apparatus and a power supply and a signal detector are coupled to each of the electrode pairs; and a processor connected to said signal detector configured to determine changes in conductance caused by a presence of said chemical and/or biological species in said phase in a proximity of each electrode pair.

30. The method according to claim 29 wherein a first and a second electrode from each pair are disposed on the first rigid architecture and a second rigid architecture, respectively, such that they substantially overlap;

the first and second rigid architecture are spaced by a spacer; and the gel component through which the phase containing the chemical and/or biological species to be separated flows is disposed between the first and second rigid architecture.

* * * * *